(12) United States Patent
Morton et al.

(10) Patent No.: US 12,239,818 B2
(45) Date of Patent: Mar. 4, 2025

(54) SYSTEM AND METHOD FOR DETECTING FLUID TYPE IN TUBING FOR FLUID INJECTOR APPARATUS

(71) Applicant: Bayer HealthCare LLC, Whippany, NJ (US)

(72) Inventors: Richard Morton, Allison Park, PA (US); Christopher Scutt, Murrysville, PA (US); Michael Spohn, Fenelton, PA (US); Randy Lee, Pittsburgh, PA (US); Mikayla Ferchaw, Pittsburgh, PA (US); Kevin Cowan, Allison Park, PA (US); Patrick Campbell, Apollo, PA (US); Andrew Naples, Mars, PA (US); William Barone, Pittsburgh, PA (US); Christopher Capone, Pittsburgh, PA (US); Curtis Pastor, Allen, TX (US); Charles Lang, Pittsburgh, PA (US); Michael Swantner, Saxonburg, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 18/560,984

(22) PCT Filed: Feb. 25, 2022

(86) PCT No.: PCT/US2022/017900
§ 371 (c)(1),
(2) Date: Nov. 15, 2023

(87) PCT Pub. No.: WO2022/265695
PCT Pub. Date: Dec. 22, 2022

(65) Prior Publication Data
US 2024/0207509 A1 Jun. 27, 2024

Related U.S. Application Data

(60) Provisional application No. 63/212,055, filed on Jun. 17, 2021.

(51) Int. Cl.
*A61M 5/145* (2006.01)
*A61M 5/00* (2006.01)
(Continued)

(52) U.S. Cl.
CPC .... *A61M 5/14546* (2013.01); *A61M 5/16827* (2013.01); *A61M 5/365* (2013.01); *A61M 2205/3306* (2013.01)

(58) Field of Classification Search
CPC .......... A61M 5/14546; A61M 5/16827; A61M 5/365; A61M 2205/3306; A61M 5/1408;
(Continued)

(56) References Cited

U.S. PATENT DOCUMENTS

| 352,715 A | 11/1886 | Sandmark |
| 508,584 A | 11/1893 | Stevens |

(Continued)

FOREIGN PATENT DOCUMENTS

| CN | 103917269 A | 7/2014 |
| CN | 105521533 A | 4/2016 |

(Continued)

OTHER PUBLICATIONS

International Preliminary Report on Patentability from PCT Application No. PCT/US2022/017900, mailed Dec. 28, 2023.
(Continued)

*Primary Examiner* — Chelsea E Stinson
*Assistant Examiner* — Hamza A Darb
(74) *Attorney, Agent, or Firm* — Joseph L. Kent; James R. Stevenson

(57) ABSTRACT

A fluid injector system includes at least one injector for pressurizing and delivering at least one fluid from at least
(Continued)

one fluid reservoir, at least one fluid path section providing fluid communication between a bulk fluid reservoir and a syringe connected to the at least one injector, and at least one sensor arranged along the at least one fluid path section. The at least one sensor includes an emitter configured to emit light through the at least one fluid path section, and a detector configured to receive the light emitted through the at least one fluid path section and generate an electrical signal based on at least one property of the received light. The fluid injector system may further include at least one processor programmed or configured to determine, based on the electrical signal generated by the detector, at least one of an identity of the at least one fluid present in the fluid path section, a concentration of the at least one fluid in the fluid path section, and at least one property of the fluid path section.

19 Claims, 23 Drawing Sheets

(51) Int. Cl.
*A61M 5/14* (2006.01)
*A61M 5/168* (2006.01)
*A61M 5/36* (2006.01)
*A61M 5/48* (2006.01)

(58) Field of Classification Search
CPC .............. A61M 5/482; A61M 5/007; A61M 2005/1403; A61M 2205/276; A61M 5/16831; A61M 2005/1402; A61M 2205/18; A61M 2205/502; A61M 2205/581; A61M 2205/584; A61M 2205/58

See application file for complete search history.

(56) References Cited

U.S. PATENT DOCUMENTS

| | | |
|---|---|---|
| 798,093 A | 8/1905 | Edward |
| 817,054 A | 4/1906 | Gay |
| 937,029 A | 10/1909 | Strong et al. |
| 945,143 A | 1/1910 | Szamek |
| 1,388,946 A | 8/1921 | Goold |
| 1,930,929 A | 10/1933 | Moses et al. |
| 2,062,285 A | 12/1936 | Bergman et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van Sciver, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Prussin et al. |
| 3,471,058 A | 10/1969 | Latham et al. |
| 3,473,524 A | 10/1969 | Drewe |
| 3,474,844 A | 10/1969 | Lindstrom et al. |
| 3,506,163 A | 4/1970 | Rauh et al. |
| 3,507,278 A | 4/1970 | Werding |
| 3,527,215 A | 9/1970 | De Witt |
| 3,557,788 A | 1/1971 | Swartz |
| 3,613,963 A | 10/1971 | Berkmuller |
| 3,618,846 A | 11/1971 | Poli |
| 3,635,444 A | 1/1972 | Potter |
| 3,671,208 A | 6/1972 | Medsker |
| 3,699,961 A | 10/1972 | Szpur |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A | 3/1975 | Harding |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett, III |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,904,239 A | 2/1990 | Winchell et al. |
| 4,952,068 A | 8/1990 | Flint |
| 4,969,879 A | 11/1990 | Lichte |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |

(56) References Cited

U.S. PATENT DOCUMENTS

| | | |
|---|---|---|
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,399,173 A | 3/1995 | Parks et al. |
| 5,431,185 A | 7/1995 | Shannon et al. |
| 5,492,147 A | 2/1996 | Challender et al. |
| 5,507,535 A | 4/1996 | McKamey et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 5,984,378 A | 11/1999 | Ostrander et al. |
| 6,054,194 A | 4/2000 | Kane |
| 6,056,724 A | 5/2000 | Lacroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 | 1/2001 | Schnell et al. |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di Scala et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans, III et al. |
| 6,773,417 B2 | 8/2004 | Fitzgibbons et al. |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Hansen |
| 7,011,650 B2 | 3/2006 | Rosoff et al. |
| 7,094,216 B2 | 8/2006 | Trombley, III et al. |
| 7,101,352 B2 | 9/2006 | Duchon et al. |
| 7,192,416 B1 | 3/2007 | Lazzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins et al. |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,666,169 B2 | 2/2010 | Cowan et al. |
| 7,686,788 B2 | 3/2010 | Freyman et al. |
| 7,766,883 B2 | 8/2010 | Rellly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,540,698 B2 | 9/2013 | Spohn et al. |
| 8,740,877 B2 | 6/2014 | Borlaug et al. |
| 8,795,240 B2 | 8/2014 | Chelak |
| 8,872,708 B2 | 10/2014 | Hill et al. |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,945,051 B2 | 2/2015 | Schriver et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |

(56) References Cited

U.S. PATENT DOCUMENTS

| | | |
|---|---|---|
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 10,933,190 B2 | 3/2021 | Berry et al. |
| 11,083,882 B2 | 8/2021 | Schrauder et al. |
| 11,207,462 B2 | 12/2021 | Cowan et al. |
| 11,389,585 B2 | 7/2022 | Spohn et al. |
| 11,413,403 B2 | 8/2022 | Yoshioka et al. |
| 11,547,793 B2 | 1/2023 | Cowan et al. |
| 2001/0004466 A1 | 6/2001 | Heinz et al. |
| 2001/0018575 A1 | 8/2001 | Lyza |
| 2002/0010596 A1 | 1/2002 | Matory |
| 2002/0147429 A1 | 10/2002 | Cowan et al. |
| 2003/0216695 A1 | 11/2003 | Yang |
| 2003/0226539 A1 | 12/2003 | Kim et al. |
| 2004/0064041 A1 | 4/2004 | Lazzaro et al. |
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2005/0113754 A1 | 5/2005 | Cowan |
| 2005/0121103 A1 | 6/2005 | Steigerwalt et al. |
| 2005/0225082 A1 | 10/2005 | Dalle et al. |
| 2006/0052794 A1 | 3/2006 | McGill et al. |
| 2006/0149213 A1 | 7/2006 | Raybuck |
| 2006/0200083 A1 | 9/2006 | Freyman et al. |
| 2007/0068964 A1 | 3/2007 | Tanaami et al. |
| 2007/0129705 A1 | 6/2007 | Trombley et al. |
| 2008/0045925 A1 | 2/2008 | Stepovich et al. |
| 2008/0086087 A1 | 4/2008 | Spohn et al. |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0218434 A1 | 9/2011 | Ziemba et al. |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0123257 A1 | 5/2012 | Stokes, Jr. et al. |
| 2012/0178629 A1 | 7/2012 | Hudson et al. |
| 2012/0209111 A1 | 8/2012 | Cowan et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1 | 2/2013 | Kirkpatrick |
| 2013/0067416 A1 | 3/2013 | Barron et al. |
| 2013/0204130 A1 | 8/2013 | McArthur et al. |
| 2013/0211248 A1 | 8/2013 | Cowan et al. |
| 2013/0281940 A1 | 10/2013 | Gelblum et al. |
| 2013/0310756 A1 | 11/2013 | Whalley et al. |
| 2014/0124087 A1 | 5/2014 | Anderson et al. |
| 2014/0261713 A1 | 9/2014 | Schriver et al. |
| 2014/0276652 A1 | 9/2014 | Gittard |
| 2014/0374353 A1 | 12/2014 | Wright et al. |
| 2015/0260325 A1 | 9/2015 | Quick |
| 2016/0030662 A1 | 2/2016 | Uber, III et al. |
| 2016/0250409 A1 | 9/2016 | Dedig et al. |
| 2017/0035974 A1 | 2/2017 | Berry et al. |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0015274 A1 | 1/2018 | Haury et al. |
| 2018/0161496 A1 | 6/2018 | Berry et al. |
| 2018/0280630 A1 | 10/2018 | Jiang et al. |
| 2018/0296755 A1 * | 10/2018 | Dahlin .............. A61M 5/16877 |
| 2018/0339146 A1 | 11/2018 | Schrauder et al. |
| 2019/0240424 A1 | 8/2019 | Yoshioka et al. |
| 2020/0164141 A1 | 5/2020 | Biermann et al. |
| 2020/0206490 A1 | 7/2020 | Bae |
| 2020/0246541 A1 | 8/2020 | Neftel et al. |
| 2021/0023298 A1 | 1/2021 | McDermott et al. |
| 2021/0146064 A1 | 5/2021 | Knutsson |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |
| 2023/0146744 A1 | 5/2023 | Cowan et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 1572266 B1 | 4/2008 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 1173662 A | 12/1969 |
| GB | 2214819 A | 9/1989 |
| GB | 2374143 A | 10/2002 |
| JP | H02-88664 | 7/1990 |
| JP | H0849598 A | 2/1996 |
| JP | H0999034 A | 4/1997 |
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | WO-2007133942 A2 * | 11/2007 ........ A61M 5/14216 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2010014654 A1 | 2/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |

(56) References Cited

FOREIGN PATENT DOCUMENTS

| | | |
|---|---|---|
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |
| WO | 2018218132 A1 | 11/2018 |
| WO | 2019046259 A1 | 3/2019 |
| WO | 2019046260 A1 | 3/2019 |
| WO | 2019046299 A1 | 3/2019 |
| WO | 2019152978 A1 | 8/2019 |
| WO | 2019204605 A1 | 10/2019 |
| WO | 2019204617 A1 | 10/2019 |
| WO | 2020055785 A1 | 3/2020 |
| WO | 2020055818 A1 | 3/2020 |
| WO | 2021050507 A1 | 3/2021 |
| WO | 2021168076 A1 | 8/2021 |
| WO | 2021173743 A1 | 9/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257667 A1 | 12/2021 |
| WO | 2021257699 A1 | 12/2021 |
| WO | 2022035791 A1 | 2/2022 |
| WO | 2022036058 A1 | 2/2022 |
| WO | 2022265695 A1 | 12/2022 |

OTHER PUBLICATIONS

International Preliminary Report on Patentability and Written Opinion mailed on Sep. 24, 2015 from corresponding PCT Application No. PCT/US2014/022629.
International Preliminary Report on Patentability and Written Opinion mailed on Sep. 2, 24015from corresponding PCT Application No. PCT/US2014/026324.
International Search Report and Written Opinion mailed Jul. 18, 2014 from corresponding PCT Application No. PCT/US2014/026324, which was filed on Mar. 13, 2014.
International Search Report and Written Opinion mailed Jul. 30, 2014 from corresponding PCT Application No. PCT/US2014/022629.
International Preliminary Report on Patentability from PCT Application No. PCT/US2020/049885, Mar. 24, 2022.
International Preliminary Report on Patentability from PCT Application No. PCT/US2021/022321, Sep. 29, 2022.
International Preliminary Report on Patentability from PCT Application No. PCT/US2021/022421, Sep. 29, 2022.
International Preliminary Report on Patentability from PCT Application No. PCT/US2021/029963, Nov. 10, 2022.
International Preliminary Report on Patentability from PCT Application No. PCT/US2021/030210, Nov. 10, 2022.
International Preliminary Report on Patentability from PCT Application No. PCT/US2021/035273, Dec. 15, 2022.
International Preliminary Report on Patentability from PCT Application No. PCT/US2021/037623, Dec. 29, 2022.
International Preliminary Report on Patentability from PCT Application No. PCT/US2021/045298, Feb. 23, 2023.
International Preliminary Report on Patentability from PCT Application No. PCT/US2021/045689, Feb. 23, 2023.
International Preliminary Report on Patentability from PCT Application No. PCT/US2021/061201, mailed Jun. 15, 2023.
International Preliminary Report on Patentability in PCT Application No. PCT/US2023/025159, mailed Sep. 4, 2023.
International Search Report and Written Opinion from PCT Application No. PCT/US2016/063448, Feb. 24, 2017.
ISR dated Aug. 19, 2022 from PCT/US2022/017812.
PCT Application No. PCT/US2023/025159 entitled "Disinfecting Cap for Fluid Path Element", filed Jun. 13, 2023.
Supplementary European Search Report from EP 14770001, Nov. 25, 2016.
UN Haluk, A New Device Preventing Air Embolism During the Angiography, Air Trap Device: An In-Vitro Experimental Air Emboli Study, Proceedings of the 2019 Design of Medical Devices Conference, 2019.

* cited by examiner

SYSTEM AND METHOD FOR DETECTING FLUID TYPE IN TUBING FOR FLUID INJECTOR APPARATUS

CROSS-REFERENCE TO RELATED APPLICATION

The present application is a U.S. national phase application under 35 U.S.C. § 371 of PCT International Application No. PCT/US2022/017900, filed Feb. 25, 2022, and claims the benefit of U.S. Provisional Patent Application No. 63/212,055, filed on Jun. 17, 2021, the disclosure disclosures of which are hereby incorporated by reference in their entirety.

BACKGROUND OF THE DISCLOSURE

Field of the Disclosure

The present disclosure is related to the field of fluid injector and apparatus for injecting contrast media for contrast enhanced medical imaging procedures. In particular, embodiments of a system and method for detecting air and fluid type (contrast and saline) and fluid concentration in a fluid tubing set of the fluid injector apparatus are described.

Description of Related Art

In many medical diagnostic and therapeutic procedures, a medical practitioner injects a patient with one or more medical fluids. In recent years, a number of injector-actuated syringes and powered fluid injectors for pressurized injection of medical fluids, such as an imaging contrast media solution (often referred to simply as "contrast"), a flushing agent, such as saline or Ringer's lactate, and other medical fluids, have been developed for use in imaging procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of fluid at a preset pressure, duration, and/or flow rate.

Typically, fluid injectors have at least one drive member, such as a piston, that connects to the syringe, for example via connection with a plunger or an engagement feature on a proximal end wall of the syringe. Alternatively, the fluid injector may include one or more peristaltic pumps for injecting the medical fluid from a fluid reservoir. The syringe may include a rigid barrel with a syringe plunger slidably disposed within the barrel. The drive members drive the plungers in a proximal and/or distal direction relative to a longitudinal axis of the barrel to draw fluid into or deliver the fluid from the syringe barrel, respectively. In certain applications, the medical fluids are injected into the vascular system at fluid pressures up to 300 psi for CT imaging procedures or up to 1200 psi, for example for CV imaging procedures.

During certain injection where both contrast and a flushing fluid are to be injected into the patient, it is important that system and user recognize which syringe includes contrast and which includes the flushing agent and to utilize the correct contrast agent to ensure accurate amounts of contrast and flushing fluid are injected at the correct point in the injection procedure to minimize or eliminate over injection of contrast, ease injection set-up, and ensure correct contrast concentrations are being used. New methods and devices are necessary to verify the type and concentration of fluids being loaded into the corresponding syringes and allow the injection system to clearly indicate which syringe contains which injection fluid, as certain injection fluids are costly and can cause patient harm if administered incorrectly.

SUMMARY OF THE DISCLOSURE

In view of the above-identified needs, the present disclosure provides systems, devices, and methods for detecting the contents in a fluid line during a medical fluid injection procedure. Certain embodiments of the present disclosure are directed to a fluid injector system. The system includes at least one injector for pressurizing and delivering at least one fluid from at least one fluid reservoir, at least one fluid path section providing fluid communication between a bulk fluid reservoir and a syringe connected to the at least one injector, and at least one sensor arranged along the at least one fluid path section. The at least one sensor includes an emitter configured to emit light through the at least one fluid path section, and a detector configured to receive the light emitted through the at least one fluid path section and generate an electrical signal based on at least one property of the received light. The system further includes at least one processor programmed or configured to determine, based on the electrical signal generated by the detector, at least one of an identity of the at least one fluid present in the fluid path section, a concentration of the at least one fluid in the fluid path section, and at least one property of the fluid path section.

In some embodiments, the emitter is arranged on a first side of the fluid path section, the detector is arranged on a second side of the fluid path section, and the second side of the fluid path section is approximately 180° opposite the first side of the fluid path section.

In some embodiments, the fluid injector system further includes a first fluid reservoir and a second fluid reservoir for delivering a first fluid and a second fluid, respectively. The system further includes a first fluid path section in fluid communication with the first fluid reservoir, a second fluid path section in fluid communication with the second fluid reservoir, and a first sensor and a second sensor. The first fluid path section is associated with the first sensor and the second fluid path section is associated with the second sensor.

In some embodiments, the fluid injector system further includes a first bulk fluid container in fluid communication with the first fluid reservoir and a second bulk fluid container in fluid communication with the second fluid reservoir. The first sensor is arranged to detect fluid entering the first fluid reservoir from the first bulk fluid container during a filling operation of the first fluid reservoir, and the second sensor is arranged to detect fluid entering the second fluid reservoir from the second bulk fluid container during a filling operation of the second fluid reservoir.

In some embodiments, the at least one processor is programmed or configured to determine, based on the electrical signals generated by the first and second sensors, that the fluid filling the first fluid reservoir was originally intended to fill the second fluid reservoir, and the fluid filling the second fluid reservoir was originally intended to fill the first fluid reservoir.

In some embodiments, the at least one processor is programmed or configured to perform an operation selected from: halting the filling operation in response to determining that the fluid filling the first fluid reservoir was originally intended to fill the second fluid reservoir, and adjusting an injection protocol to ensure that injection parameters are updated to switch the identity of the first fluid reservoir and the second fluid reservoir so that first fluid is associated with the first fluid reservoir and the second fluid is associated with the second fluid reservoir.

In some embodiments, the at least one processor is programmed or configured to alter the injection protocol by configuring the first fluid reservoir to inject the fluid originally intended to be injected by the second fluid reservoir; and configuring the second fluid reservoir to inject the fluid originally intended to be injected by the first fluid reservoir.

In some embodiments, the at least one processor is programmed or configured to adjust a display of a graphical user interface or to illuminate a light source associated with the fluid reservoirs to indicate that the first fluid reservoir contains the fluid originally intended to be injected by the second fluid reservoir, and that the second fluid reservoir contains the fluid originally intended to be injected by the first fluid reservoir.

In some embodiments, the fluid injector system, further includes a manifold. The manifold includes the at least one fluid path section, an inlet port connected to a syringe tip of the at least one fluid reservoir, an outlet port connected to a patient line, and a fill port connected to a bulk fluid container.

In some embodiments, the least one processor is programmed or configured to determine, based on at least one of identity of the fluid and concentration of the fluid in the at least one fluid path section, an optimal fill rate of the at least one fluid reservoir.

In some embodiments, the optimal fill rate includes a fastest speed of filling the at least one fluid reservoir that minimizes introduction of bubbles into the fluid as it enters the at least one fluid reservoir.

In some embodiments, the detector is configured to output a first voltage signal when the at least one fluid path section contains contrast media. The detector is configured to output a second voltage signal when the fluid path section contains saline. The at least one processor is programmed or configured to determine the identity of the injection fluid in the at least one fluid path section based on a difference between the first voltage signal and the second voltage signal.

In some embodiments, the detector is configured to output a third voltage signal when the at least one fluid path section contains air. The at least one processor is programmed or configured to determine that air is in the at least one fluid path section based on a difference between the third voltage signal, the first voltage signal, and the second voltage signal.

In some embodiments, when the detector determines that the fluid path section contains air, the detector is configured to provide an alert to a user that the bulk fluid reservoir is empty.

In some embodiments, the at least one processor is programmed or configured to determine a concentration of a contrast media in the at least one fluid path section based on the electrical signal generated by the at least one sensor and increase a ratio of saline injected during an injection procedure to dilute the concentration of the contrast media delivered to the patient.

In some embodiments, the at least one processor is programmed or configured to determine a concentration of a contrast media in the fluid path section based on the electrical signal generated by the at least one sensor and reduce an injection rate of saline during an injection procedure to increase the concentration of the contrast media delivered to the patient.

In some embodiments, the emitter is arranged to emit light perpendicular to a fluid flow direction through the at least one fluid path section.

In some embodiments, the at least one processor is programmed or configured to determine, based on the electrical signal, that the at least one fluid path section is present between the emitter and the detector.

In some embodiments, the emitter is configured to emit light on the ultraviolet spectrum. The emitted light may have a wavelength from about 300 nm to about 400 nm.

In some embodiments, the emitter is configured to emit light on the infrared spectrum. The emitted light may have a wavelength from about 700 nm to about 2000 nm.

In some embodiments, the emitter is configured to emit light on the visible spectrum. The emitted light may have a wavelength from about 400 nm to about 700 nm.

In some embodiments, the at least one processor is programmed or configured to drive the emitter at a first emitter current, the first emitter current is configured to saturate the detector if a first fluid is present in the fluid path section.

In some embodiments, the at least one processor is programmed or configured to drive the emitter at a second emitter current greater than the first emitter current, the second emitter current is configured to saturate the detector if a second fluid is present in the fluid path section.

Other embodiments of the present disclosure are direct to a method for determining one or more fluid properties of a fluid flowing in at least one fluid path section of a fluid injector system. The method includes emitting light from an emitter of at least one sensor through the at least one fluid path section, detecting with a detector of the first proximal sensor the light that has passed through the at least one fluid path section, and determining, based on an electrical signal generated by the detector, at least one of an identity of an injection fluid present in the fluid path set, a concentration of the injection fluid in the fluid path set, and at least one property of the fluid path section.

In some embodiments, the emitter is arranged on a first side of the fluid path section, the detector is arranged on a second side of the fluid path section, and the second side of the fluid path section is approximately 180° opposite the first side of the fluid path section.

In some embodiments, the fluid injector system includes a first fluid reservoir and a second fluid reservoir for delivering a first fluid and a second fluid, respectively, a first fluid path section in fluid communication with the first fluid reservoir, a second fluid path section in fluid communication with the second fluid reservoir, and a first sensor and a second sensor. The first fluid path section is associated with the first sensor and the second fluid path section is associated with the second sensor.

In some embodiments, the fluid injector system further includes a first bulk fluid container in fluid communication with the first fluid reservoir, and a second bulk fluid container in fluid communication with the second fluid reservoir. The first sensor is arranged to detect fluid entering the first fluid reservoir during a filling operation of the first fluid reservoir, and the second sensor is arranged to detect fluid entering the second fluid reservoir during a filling operation of the second fluid reservoir.

In some embodiments, the method further includes determining, based on the electrical signals generated by the first and second sensors, that the fluid filling the first fluid reservoir was originally intended to fill the second fluid reservoir, and the fluid filling the second fluid reservoir was originally intended to fill the first fluid reservoir.

In some embodiments, the method further includes halting the fill operation in response to determining that the fluid filling the first fluid reservoir was originally intended to fill the second fluid reservoir.

In some embodiments, the method further includes adjusting an injection protocol to ensure that injection parameters are updated to switch the identity of the first fluid reservoir and the second fluid reservoir so that first fluid is associated with the first fluid reservoir and the second fluid is associated with the second fluid reservoir.

In some embodiments, the method further includes altering an injection protocol by configuring the first fluid reservoir to inject the fluid originally intended to be injected by the second fluid reservoir and configuring the second fluid reservoir to inject the fluid originally intended to be injected by the first fluid reservoir.

In some embodiments, the method further includes adjusting a display of a graphical user interface or illuminating a light source associated with the fluid reservoirs to indicate that the first fluid reservoir contains the fluid originally intended to be injected by the second fluid reservoir, and that the second fluid reservoir contains the fluid originally intended to be injected by the first fluid reservoir.

In some embodiments, the fluid injector system further includes a manifold. The manifold includes the at least one fluid path section, an inlet port connected to a syringe tip of the at least one fluid reservoir, an outlet port connected to a patient line, and a fill port connected to a bulk fluid container.

In some embodiments, the method further includes determining, based on at least one of identity of the fluid and concentration of the fluid in the at least one fluid path section, an optimal fill rate of the at least one fluid reservoir.

In some embodiments, the optimal fill rate includes a fastest speed of filling the at least one fluid reservoir that minimizes introduction of bubbles into the fluid as it enters the at least one fluid reservoir.

In some embodiments, the detector is configured to output a first voltage signal when the at least one fluid path section contains contrast media. The detector is configured to output a second voltage signal when the fluid path section contains saline. The method further includes determining the identity of the injection fluid in the at least one fluid path section based on a difference between the first voltage signal and the second voltage signal.

In some embodiments, the detector is configured to output a third voltage signal when the at least one fluid path section contains air. The method further includes determining that air is in the fluid path section based on a difference between the third voltage signal, the first voltage signal, and the second voltage signal.

In some embodiments, the method further includes providing an alert to a user that the bulk fluid reservoir is empty when the detector determines that the fluid path section contains air.

In some embodiments, the method further includes determining a concentration of a contrast media in the at least one fluid path section based on the electrical signal generated by the at least one sensor; and increasing a ratio of saline injected during an injection procedure to dilute the concentration of the contrast media delivered to the patient.

In some embodiments, the method further includes determining a concentration of a contrast media in the at least one fluid path section based on the electrical signal generated by the at least one sensor; and reducing an injection rate of saline during an injection procedure to increase the concentration of the contrast media delivered to the patient.

In some embodiments, the emitter is arranged to emit light perpendicular to a fluid flow direction through the at least one fluid path section.

In some embodiments, the method further includes determining, based on the electrical signal, that the at least one fluid path section is present between the emitter and the detector.

In some embodiments, the emitter is configured to emit light on the ultraviolet spectrum. The emitted light may have a wavelength from about 300 nm to about 400 nm.

In some embodiments, the emitter is configured to emit light on the infrared spectrum. The emitted light may have a wavelength from about 700 nm to about 2000 nm.

In some embodiments, the emitter is configured to emit light on the visible spectrum. The emitted light may have a wavelength from about 400 nm to about 700 nm.

In some embodiments, the method further includes driving the emitter at a first emitter current, the first emitter current is configured to saturate the detector if a first fluid is present in the fluid path section.

In some embodiments, the method further includes driving the emitter at a second emitter current greater than the first emitter current, the second emitter current is configured to saturate the detector if a second fluid is present in the fluid path section.

Further aspects or examples of the present disclosure are described in the following numbered clauses:

Clause 1. A fluid injector system, comprising: at least one injector for pressurizing and delivering at least one fluid from at least one fluid reservoir: at least one fluid path section providing fluid communication between a bulk fluid reservoir and a syringe connected to the at least one injector: at least one sensor arranged along the at least one fluid path section, the at least one sensor comprising: an emitter configured to emit light through the at least one fluid path section; and a detector configured to receive the light emitted through the at least one fluid path section and generate an electrical signal based on at least one property of the received light; and at least one processor programmed or configured to determine, based on the electrical signal generated by the detector, at least one of: an identity of the at least one fluid present in the fluid path section: a concentration of the at least one fluid in the fluid path section; and at least one property of the fluid path section.

Clause 2. The fluid injector system of clause 1, wherein the emitter is arranged on a first side of the fluid path section, wherein the detector is arranged on a second side of the fluid path section, and wherein the second side of the fluid path section is approximately 180° opposite the first side of the fluid path section.

Clause 3. The fluid injector system of clause 1 or 2, further comprising: a first fluid reservoir and a second fluid reservoir for delivering a first fluid and a second fluid, respectively; a first fluid path section in fluid communication with the first fluid reservoir: a second fluid path section in fluid communication with the second fluid reservoir; and a first sensor and a second sensor, wherein the first fluid path section is associated with the first sensor and the second fluid path section is associated with the second sensor.

Clause 4. The fluid injector system of any of clauses 1 to 3, further comprising: a first bulk fluid container in fluid communication with the first fluid reservoir; and a second bulk fluid container in fluid communication with the second fluid reservoir, wherein the first sensor is arranged to detect fluid entering the first fluid reservoir from the first bulk fluid container during a filling operation of the first fluid reservoir, and wherein the second sensor is arranged to detect fluid entering the second fluid reservoir from the second bulk fluid container during a filling operation of the second fluid reservoir.

Clause 5. The fluid injector system of any of clauses 1 to 4, wherein the at least one processor is programmed or configured to determine, based on the electrical signals generated by the first and second sensors, that: the fluid filling the first fluid reservoir was originally intended to fill the second fluid reservoir; and the fluid filling the second fluid reservoir was originally intended to fill the first fluid reservoir.

Clause 6. The fluid injector system of any of clauses 1 to 5, wherein the at least one processor is programmed or configured to perform an operation selected from: halting the filling operation in response to determining that the fluid filling the first fluid reservoir was originally intended to fill the second fluid reservoir; and adjusting an injection protocol to ensure that injection parameters are updated to switch the identity of the first fluid reservoir and the second fluid reservoir so that first fluid is associated with the first fluid reservoir and the second fluid is associated with the second fluid reservoir.

Clause 7. The fluid injector system of any of clauses 1 to 6, wherein the at least one processor is programmed or configured to alter the injection protocol by configuring the first fluid reservoir to inject the fluid originally intended to be injected by the second fluid reservoir and configuring the second fluid reservoir to inject the fluid originally intended to be injected by the first fluid reservoir.

Clause 8. The fluid injector system of any of clauses 1 to 7, wherein the at least one processor is programmed or configured to adjust a display of a graphical user interface or to illuminate a light source associated with the fluid reservoirs to indicate that the first fluid reservoir contains the fluid originally intended to be injected by the second fluid reservoir, and that the second fluid reservoir contains the fluid originally intended to be injected by the first fluid reservoir.

Clause 9. The fluid injector system of any of clauses 1 to 8, further comprising a manifold, wherein the manifold comprises: the at least one fluid path section: an inlet port connected to a syringe tip of the at least one fluid reservoir: an outlet port connected to a patient line; and a fill port connected to a bulk fluid container.

Clause 10. The fluid injector system of any of clauses 1 to 9, wherein the least one processor is programmed or configured to determine, based on at least one of identity of the fluid and concentration of the fluid in the at least one fluid path section, an optimal fill rate of the at least one fluid reservoir.

Clause 11. The fluid injector system of any of clauses 1 to 10, wherein the optimal fill rate comprises a fastest speed of filling the at least one fluid reservoir that minimizes introduction of bubbles into the fluid as it enters the at least one fluid reservoir.

Clause 12. The fluid injector system of any of clauses 1 to 11, wherein the detector is configured to output a first voltage signal when the at least one fluid path section contains contrast media, wherein the detector is configured to output a second voltage signal when the fluid path section contains saline, and wherein the at least one processor is programmed or configured to determine the identity of the injection fluid in the at least one fluid path section based on a difference between the first voltage signal and the second voltage signal.

Clause 13. The fluid injector system of any of clauses 1 to 12, wherein the detector is configured to output a third voltage signal when the at least one fluid path section contains air, and wherein the at least one processor is programmed or configured to determine that air is in the at least one fluid path section based on a difference between the third voltage signal, the first voltage signal, and the second voltage signal.

Clause 14. The fluid injector system of any of clauses 1 to 13, wherein when the detector determines that the fluid path section contains air, the detector is configured to provide an alert to a user that the bulk fluid reservoir is empty.

Clause 15. The fluid injector system of any of clauses 1 to 14, wherein the at least one processor is programmed or configured to: determine a concentration of a contrast media in the at least one fluid path section based on the electrical signal generated by the at least one sensor and increase a ratio of saline injected during an injection procedure to dilute the concentration of the contrast media delivered to the patient.

Clause 16. The fluid injector system of any of clauses 1 to 15, wherein the at least one processor is programmed or configured to: determine a concentration of a contrast media in the fluid path section based on the electrical signal generated by the at least one sensor and reduce an injection rate of saline during an injection procedure to increase the concentration of the contrast media delivered to the patient.

Clause 17. The fluid injector system of any of clauses 1 to 16, wherein the emitter is arranged to emit light perpendicular to a fluid flow direction through the at least one fluid path section.

Clause 18. The fluid injector system of any of clauses 1 to 17, wherein the at least one processor is programmed or configured to determine, based on the electrical signal, that the at least one fluid path section is present between the emitter and the detector.

Clause 19. The fluid injector system of any of clauses 1 to 18, wherein the emitter is configured to emit light on the ultraviolet spectrum.

Clause 20. The fluid injector system of any of clauses 1 to 19, wherein the emitted light has a wavelength from about 300 nm to about 400 nm.

Clause 21. The fluid injector system of any of clauses 1 to 20, wherein the emitter is configured to emit light on the infrared spectrum.

Clause 22. The fluid injector system of any of clauses 1 to 21, wherein the emitted light has a wavelength from about 700 nm to about 2000 nm.

Clause 23. The fluid injector system of any of clauses 1 to 22, wherein the emitter is configured to emit light on the visible spectrum.

Clause 24. The fluid injector system of any of clauses 1 to 23, wherein the emitted light has a wavelength from about 400 nm to about 700 nm.

Clause 25. The fluid injector system of any of clauses 1 to 24, wherein the at least one processor is programmed or configured to drive the emitter at a first emitter current, wherein the first emitter current is configured to saturate the detector if a first fluid is present in the fluid path section.

Clause 26. The fluid injector system of any of clauses 1 to 25, wherein the at least one processor is programmed or configured to drive the emitter at a second emitter current greater than the first emitter current, wherein the second emitter current is configured to saturate the detector if a second fluid is present in the fluid path section.

Clause 27. A method for determining one or more fluid properties of a fluid flowing in at least one fluid path section of a fluid injector system, the method comprising: emitting light from an emitter of at least one sensor through the at least one fluid path section: detecting with a detector of the first proximal sensor the light that has passed through the at least one fluid path section: determining, based on an electrical signal generated by the detector, at least one of: an identity of an injection fluid present in the fluid path set: a concentration of the injection fluid in the fluid path set; and at least one property of the fluid path section.

Clause 28. The method of clause 27, wherein the emitter is arranged on a first side of the fluid path section, wherein the detector is arranged on a second side of the fluid path section, and wherein the second side of the fluid path section is approximately 180° opposite the first side of the fluid path section.

Clause 29. The method of clause 27 or 28, wherein the fluid injector system comprises: a first fluid reservoir and a second fluid reservoir for delivering a first fluid and a second fluid, respectively; a first fluid path section in fluid communication with the first fluid reservoir; a second fluid path section in fluid communication with the second fluid reservoir; and a first sensor and a second sensor, wherein the first fluid path section is associated with the first sensor and the second fluid path section is associated with the second sensor.

Clause 30. The method of any of clauses 27 to 29, wherein the fluid injector system further comprises: a first bulk fluid container in fluid communication with the first fluid reservoir; and a second bulk fluid container in fluid communication with the second fluid reservoir, wherein the first sensor is arranged to detect fluid entering the first fluid reservoir during a filling operation of the first fluid reservoir, and wherein the second sensor is arranged to detect fluid entering the second fluid reservoir during a filling operation of the second fluid reservoir.

Clause 31. The method of any of clauses 27 to 30, further comprising: determining, based on the electrical signals generated by the first and second sensors, that: the fluid filling the first fluid reservoir was originally intended to fill the second fluid reservoir; and the fluid filling the second fluid reservoir was originally intended to fill the first fluid reservoir.

Clause 32. The method of any of clauses 27 to 31, further comprising: halting the fill operation in response to determining that the fluid filling the first fluid reservoir was originally intended to fill the second fluid reservoir.

Clause 33. The method of any of clauses 27 to 32, further comprising: adjusting an injection protocol to ensure that injection parameters are updated to switch the identity of the first fluid reservoir and the second fluid reservoir so that first fluid is associated with the first fluid reservoir and the second fluid is associated with the second fluid reservoir.

Clause 34. The method of any of clauses 27 to 33, further comprising: altering an injection protocol by configuring the first fluid reservoir to inject the fluid originally intended to be injected by the second fluid reservoir and configuring the second fluid reservoir to inject the fluid originally intended to be injected by the first fluid reservoir.

Clause 35. The method of any of clauses 27 to 34, further comprising: adjusting a display of a graphical user interface or illuminating a light source associated with the fluid reservoirs to indicate that the first fluid reservoir contains the fluid originally intended to be injected by the second fluid reservoir, and that the second fluid reservoir contains the fluid originally intended to be injected by the first fluid reservoir Clause 36. The method of any of clauses 27 to 35, wherein the fluid injector system further comprises a manifold, wherein the manifold comprises: the at least one fluid path section: an inlet port connected to a syringe tip of the at least one fluid reservoir: an outlet port connected to a patient line; and a fill port connected to a bulk fluid container.

Clause 37. The method of any of clauses 27 to 36, further comprising: determining, based on at least one of identity of the fluid and concentration of the fluid in the at least one fluid path section, an optimal fill rate of the at least one fluid reservoir.

Clause 38. The method of any of clauses 27 to 37, wherein the optimal fill rate comprises a fastest speed of filling the at least one fluid reservoir that minimizes introduction of bubbles into the fluid as it enters the at least one fluid reservoir.

Clause 39. The method of any of clauses 27 to 38, wherein the detector is configured to output a first voltage signal when the at least one fluid path section contains contrast media wherein the detector is configured to output a second voltage signal when the fluid path section contains saline, and wherein the method further comprises determining the identity of the injection fluid in the at least one fluid path section based on a difference between the first voltage signal and the second voltage signal.

Clause 40. The method of any of clauses 27 to 39, wherein the detector is configured to output a third voltage signal when the at least one fluid path section contains air, and wherein the method further comprises determining that air is in the fluid path section based on a difference between the third voltage signal, the first voltage signal, and the second voltage signal.

Clause 41. The method of any of clauses 27 to 40, further comprising: provide an alert to a user that the bulk fluid reservoir is empty when the detector determines that the fluid path section contains air.

Clause 42. The method of any of clauses 27 to 41 further comprising: determining a concentration of a contrast media in the at least one fluid path section based on the electrical signal generated by the at least one sensor and increasing a ratio of saline injected during an injection procedure to dilute the concentration of the contrast media delivered to the patient.

Clause 43. The method of any of clauses 27 to 42, further comprising: determining a concentration of a contrast media in the at least one fluid path section based on the electrical signal generated by the at least one sensor and reducing an injection rate of saline during an injection procedure to increase the concentration of the contrast media delivered to the patient.

Clause 44. The method of any of clauses 23 to 43, wherein the emitter is arranged to emit light perpendicular to a fluid flow direction through the at least one fluid path section.

Clause 45. The method of any of clauses 27 to 44, further comprising: determining, based on the electrical signal, that the at least one fluid path section is present between the emitter and the detector.

Clause 46. The method of any of clauses 27 to 45, wherein the emitter is configured to emit light on the ultraviolet spectrum.

Clause 47. The method of any of clauses 27 to 46, wherein the emitted light has a wavelength from about 300 nm to about 400 nm.

Clause 48. The method of any of clauses 27 to 47, wherein the emitter is configured to emit light on the infrared spectrum.

Clause 49. The method of any of clauses 27 to 48, wherein the emitted light has a wavelength from about 700 nm to about 2000 nm.

Clause 50. The method of any of clauses 27 to 49, wherein the emitter is configured to emit light on the visible spectrum.

Clause 51. The method of any of clauses 27 to 50, wherein the emitted light has a wavelength from about 400 nm to about 700 nm.

Clause 52. The method of any of clauses 27 to 51, further comprising: driving the emitter at a first emitter current, wherein the first emitter current is configured to saturate the detector if a first fluid is present in the fluid path section.

Clause 53. The fluid injector system of any of clauses 27 to 52, further comprising: driving the emitter at a second emitter current greater than the first emitter current, wherein the second emitter current is configured to saturate the detector if a second fluid is present in the fluid path section.

Further details and advantages of the various examples described in detail herein will become clear upon reviewing the following detailed description of the various examples in conjunction with the accompanying drawing figures.

DETAILED DESCRIPTION

Figure 1:
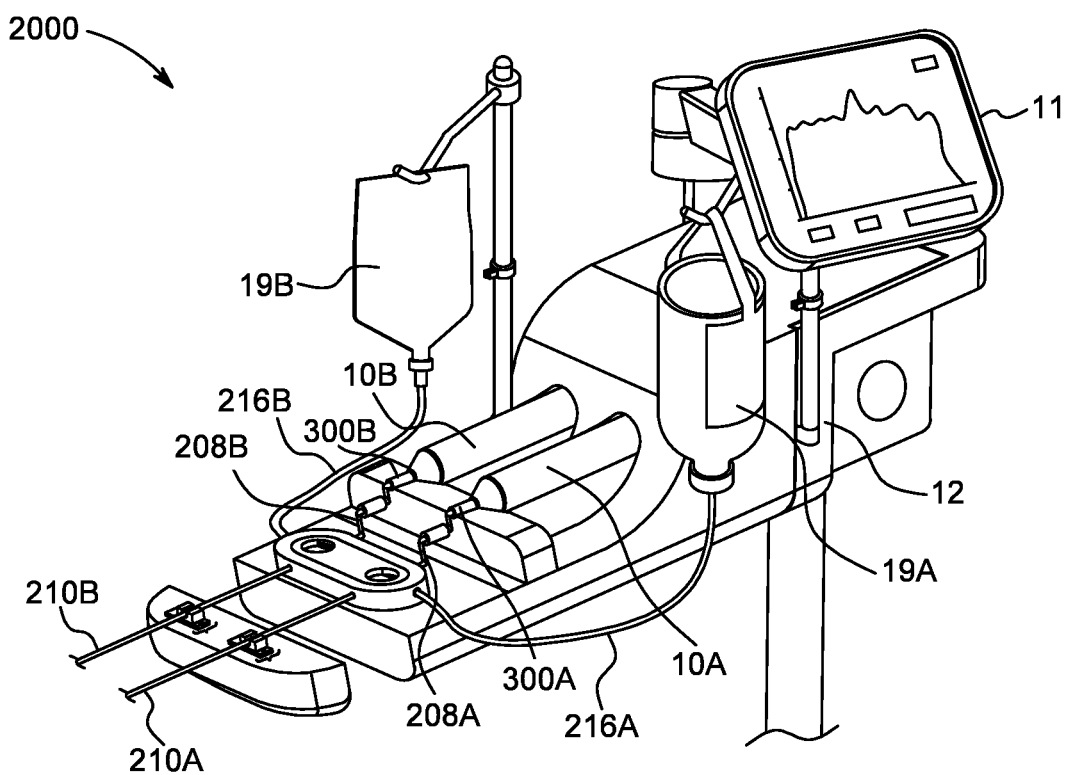
FIG. 1 is a perspective view of a fluid injector system according to an embodiment of the present disclosure.

As used herein, the singular form of "a", "an", and "the" include plural referents unless the context clearly dictates otherwise. Spatial or directional terms, such as "left", "right", "inner", "outer", "above", "below", and the like, relate to the invention as shown in the drawing figures and are not to be considered as limiting, as the invention can assume various alternative orientations.

All numbers used in the specification and claims are to be understood as being modified in all instances by the term "about". The term "about" is meant to include plus or minus twenty-five percent of the stated value, such as plus or minus ten percent of the stated value. However, this should not be considered as limiting to any analysis of the values under the doctrine of equivalents. Unless otherwise indicated, all ranges or ratios disclosed herein are to be understood to encompass the beginning and ending values and any and all subranges or sub-ratios subsumed therein. For example, a stated range or ratio of "1 to 10" should be considered to include any and all subranges or sub-ratios between (and inclusive of) the minimum value of 1 and the maximum value of 10; that is, all subranges or sub-ratios beginning with a minimum value of 1 or more and ending with a maximum value of 10 or less. The ranges and/or ratios disclosed herein represent the average values over the specified range and/or ratio. The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to". The term "not greater than" is synonymous with "less than or equal to". As used herein, "at least one of" is synonymous with "one or more of". For example, the phrase "at least one of A, B, and C" means any one of A. B, or C, or any combination of any two or more of A, B, or C. For example, "at least one of A, B, and C" includes A alone; or B alone; or C alone; or A and B; or A and C; or B and C; or all of A, B, and C. The term "includes" is synonymous with "comprises".

When used in relation to a syringe, the term "proximal" refers to a portion of a syringe nearest a piston element for engaging with an end wall of the syringe and delivering fluid from a syringe. When used in relation to a fluid path, the term "proximal" refers to a portion of the fluid path nearest to an injector system when the fluid path is connecting with the injector system. When used in relation to a syringe, the term "distal" refers to a portion of a syringe nearest to a delivery nozzle. When used in relation to a fluid path, the term "distal" refers to a portion of the fluid path nearest to a patient when the fluid path is connected with an injector system. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of the syringe extending between the proximal and distal ends.

It is to be understood that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

Figure 2:
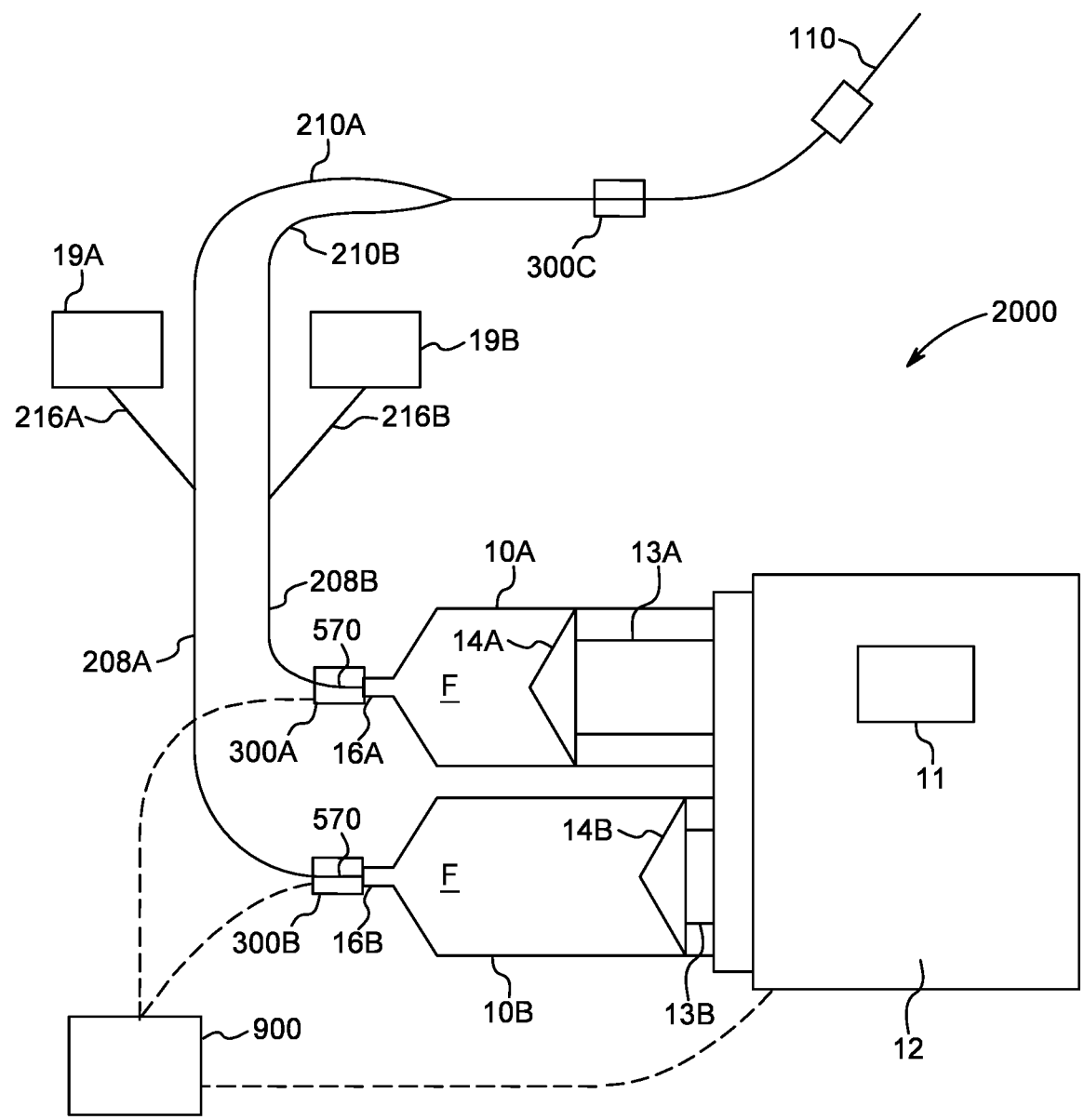
FIG. 2 is a schematic view of a fluid injector system according to an embodiment of the present disclosure.

Referring to the drawings in which like reference characters refer to like parts throughout the several views thereof, the present disclosure provides systems, components devices, and methods for detecting and analyzing fluid content of a fluid path section during a fluid fill operation. Referring first to FIGS. 1 and 2, embodiments of a dual syringe fluid injector system 2000 are illustrated. The fluid injector system 2000 is configured for injection of two medical fluids from respective fluid reservoirs 10A, 10B, which are illustrated as syringes in the accompanying drawings. In some embodiments, the first fluid reservoir 10A contains an imaging contrast media for an angiography (CV), MRI, PET, or computed tomography (CT) injection procedure, and the second fluid reservoir 10B contains a flushing fluid, such as saline or Ringer's lactate. As will be understood by one of skill in the art, contrast fluids are typically an aqueous solution of a contrast agent compound at a defined concentration. Various contrast agent compounds at different concentrations are known in the art. The fluids are injected from fluid reservoirs 10A, 10B through a series of fluid path elements connecting the fluid reservoirs 10A, 10B to a catheter 110 inserted into the vasculature system of a patient. The fluid injector system 2000 may further include bulk fluid containers 19A and 19B for filling and refilling the respective syringes 10A, 10B with imaging contrast media and flushing fluid, respectively. The system 2000 includes a fluid path set including a first syringe line 208A in fluid communication with a tip or nozzle 16A of the first syringe 10A, a first fill line 216A in fluid communication with the first bulk fluid container 19A, and a first patient line 210A in fluid communication with the catheter 110. In some embodiments, the first syringe line 208A, the first fill line 216A, and/or the first patient line 210A are fluidly connected at a manifold or T-connection (see, e.g. FIGS. 6 and 24). The fluid path set further includes a syringe line 208B in fluid communication with a tip or nozzle 16B of the second syringe 10B, a fill line 216B in fluid communication with the second bulk fluid container 19B, and a patient line 210B in fluid communication with the catheter 110. In some embodiments, the syringe line 208B, the fill line 216B, and/or the patient line 210B are fluidly connected at the manifold or T-connection (see, e.g. FIGS. 6 and 24). The arrangement of the fluid path set allows fluid to be drawn from the first bulk fluid container 19A into the first syringe 10A via the first fill line 216A and the first syringe line 208A. Fluid can be injected from the first syringe 10A to the patient via the first syringe line 208A, the patient line 210A, and the catheter 110. Similarly, fluid may be drawn from the second bulk fluid container 19B into the second syringe 10B via the second fill line 216B and the second syringe line 208B. Fluid can be injected from the second syringe 10B to the patient via the second syringe line 208B, the second patient line 210B, and the catheter 110. The syringe lines 208A, 208B, the fill lines 216A, 216B, and the outlet lines 210A, 210B may be made of flexible tubing, although various portions thereof, for example luer connectors, sensor regions and mixing chambers may be rigid. While the fluid injector 12 illustrated in FIGS. 1 and 2 is shown with a first contrast syringe and a second flushing fluid syringe, in certain injection procedures, only contrast may be used, with no associated flushing fluid. According to these embodiments, the fluid injector 12 may be engaged with only a first syringe 10A and associated first bulk reservoir 19A and fluid path components for injecting the contrast into a patient. The flush side of the fluid injector 12 may be left empty during such a single fluid injection procedure. Alternatively, a fluid injector (not shown) configured for engagement with only a single syringe may utilize the various embodiments of sensor modules and methods described herein.

Further details and examples of suitable nonlimiting powered injector systems, including syringes, tubing and fluid path components, shut-off valves, pinch valves, controllers, and air detectors, are described in U.S. Pat. Nos. 5,383,858; 7,553,294; 7,666,169; 8,945,051; 10,022,493; and 10,507,319, and International PCT Application Nos. PCT/US2013/061275; PCT/US2018/034613; PCT/US2020/049885; PCT/US2021/035273; PCT/US2021/029963; PCT/US2021/018523; PCT/US2021/037623; PCT/US2021/037574; and PCT/US2021/045298, the disclosures of which are hereby incorporated by reference in their entireties.

With continued reference to FIGS. 1 and 2, the injector system 2000 includes a first piston 13A and a second piston 13B respectively associated with each of the syringes 10A, 10B. Each of the pistons 13A, 13B is configured to drive a respective plunger 14A, 14B within a barrel of the respective syringe 10A, 10B. The fluid injector system 2000 includes a controller 900 in electronic communication with various components of the system 2000 to execute an injection procedure. In particular, the controller 900 may include at least one processor programmed or configured to actuate the pistons 13A, 13B and various other components of the injector system 2000 to deliver medical fluids according to a programmed protocol for an injection procedure, including, for example, monitoring at least one fluid property of one or more fluids being drawn into syringes 10A, 10B and determining at least one of fluid identity and fluid concentration. The controller 900 may then adjust at least one parameter of the injection protocol based on the at least one of fluid identity and fluid concentration, such as switching the syringe identity in the injection protocol so that the correct fluid is identified with the correct syringe 10 and correct injection parameters are utilized, altering a display so that the syringe image on the display correctly represents the correct fluid in the syringe, switching a color of one or more light emitters (such as an LED light) associated with the syringe to display the correct light color associated with the correct fluid type (e.g., blue for saline, green for contrast, red for air), indicate on a display the concentration of the contrast agent, adjust an injection protocol to inject a correct ratio of contrast and saline when an incorrect contrast concentration has been loaded into the contrast syringe, and provide an alert to the user that one or more errors has occurred during a fluid fill operation, such as incorrect fluid filled into the syringe, bulk fluid container is empty as only air has been drawn into the syringe, incorrect contrast concentration, changed injection protocol, and the like. The controller 900 may include computer readable media, such as memory, on which one or more injection protocols may be stored for execution by the at least one processor. Controller 900 is configured to actuate pistons 13A, 13B to reciprocatively move the plungers 14A, 14B within syringes 10A, 10B and thereby execute and halt an injection procedure. The fluid injector system 2000 may further include at least one graphical user interface (GUI) 11 through which an operator can interact with the controller 900 to view status of and control an injection procedure. In an analogous manner, if the fluid injection system 2000 includes one or more pumps, such as a peristaltic pump, the associated controller 900 may operate the various components of the fluid injector, such as the air sensor modules described herein, to ensure a correct fluid type is flowing through the correct fluid path elements based on an associated bulk fluid container, and if the fluid type is not correct, controller 900 may make the necessary adjustments and notifications to the injection protocol based on the actual fluid identified with the specific fluid pump.

Controller 900 may be programmed or configured to execute a filling operation during which the piston 13A, 13B associated with each syringe 10A, 10B is withdrawn toward a proximal end of syringe 10A, 10B to draw injection fluid F (e.g. imaging contrast media or flushing fluid) into syringes 10A, 10B from bulk fluid containers 19A, 19B, respectively. During such a filling operation, controller 900 may be programmed or configured to selectively actuate various valves, stopcocks, or clamps (such as pinch clamps) to establish fluid communication between the respective syringes 10A, 10B and the bulk fluid containers 19A. 19B via the fill lines 216A and 216B to control filling of the syringes 10A, 10B with the appropriate injection fluid F. As described herein, during the filling operation the fluid flowing through fill lines 216A, 216B is monitored by fluid sensors described herein to identify the one or more properties of the fluid in the fill line 216A or 216B and, if necessary, controller 900 may make the necessary adjustments to the system, injection protocol, etc., or alert a user based on the identification of the one or more properties of the fluid in fill line 216A or 216B.

After the filling operation and a priming operation (where excess air is removed from the syringe and various fluid path elements by flowing fluid from the syringe through the fluid path elements), the controller 900 may be programmed or configured to execute a fluid delivery operation during which the piston 13A, 13B associated with one or both of the syringes 10A, 10B is moved toward a distal end of the syringe to inject injection fluid F into the first patient line 210A and the second patient line 210B, respectively, at a specified flow rate and time to deliver a desired amount of fluid F. The controller 900 may be programmed or configured to selectively actuate various valves, stopcocks, and/or pinch clamps to establish fluid communication between the syringes 10A, 10B and the patient, via the patient lines 210A. 210B. The patient lines 210A, 210B ultimately merge before connecting to the catheter 110, for example at a turbulent mixing chamber as described in PCT International Application No. PCT/US2021/019507, the disclosure of which is incorporated herein in its entirety.

According to various embodiments, the system 2000 includes one or more sensors and/or sensor modules configured for detecting air and/or fluid in the fluid path elements associated with each syringe 10A, 10B, for example, fill lines 216A, 216B. As shown in FIGS. 1 and 2, a first sensor module 300A is arranged to be in operative communication with the first syringe tip 16A, and a second sensor module 300B is arranged to be in operative communication with the second syringe tip 16B. Alternatively or additionally, the first and second sensor modules 300A, 300B may be associated with the fill lines 216A, 216B. The sensor modules 300A, 300B are in electronic communication with the controller 900 so that the controller 900 can determine at least one property of a fluid content of a fluid path section 570) (associated with fluid lines 208A, 208B, 216A, and/or 216B) based on signals transmitted by the sensor modules 300A, 300B. For example, based on the signals transmitted by the sensor modules 300A, 300B, the controller 900 may be configured to determine an identity of the fluid in the fluid path section 570, a concentration of a medical fluid in the fluid path section 570, the presence of air in the fluid path section 570, a priming status of the fluid path section 570, a property of the fluid path section (e.g. absorption, refractory index, tubing size, and/or manufacturing defect), and combinations of any thereof. FIGS. 1 and 2 show the sensor modules 300A, 300B associated with the syringe tips 16A, 16B. However, in other embodiments, the sensor modules 300A, 300B may be associated with essentially any component of the fluid path set, including the syringe lines 208A, 208B, the fill lines 216A. 216B, or the patient lines 210A, 210B. In some embodiments, the system 2000 may further include a third sensor module 300C, functionally analogous to the first and second sensor modules 300A, 300B, downstream of a merge point of the patient lines 210A, 210B.

Figure 3:
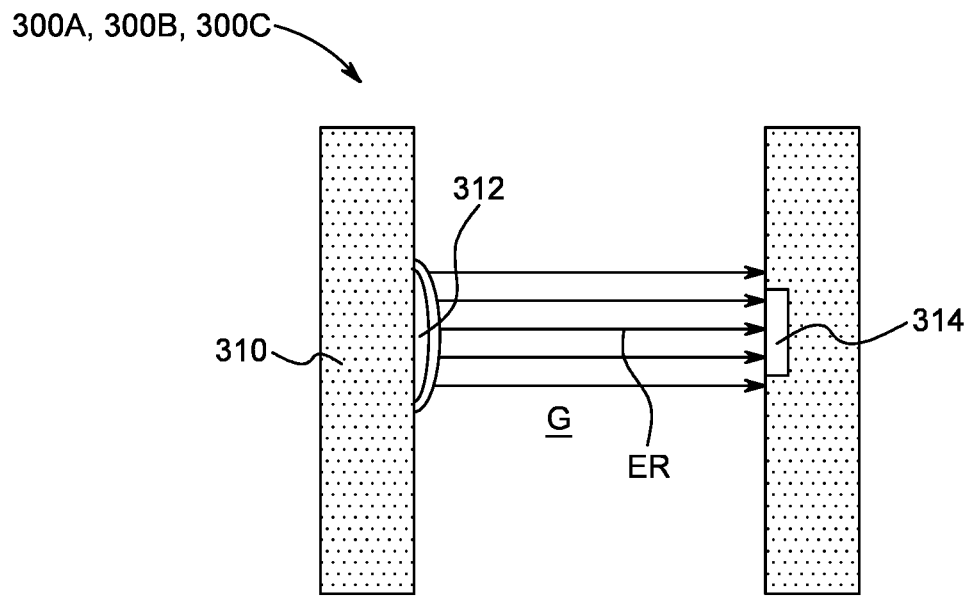
FIG. 3 is a front cross-sectional view of a sensor module according to an embodiment of the present disclosure.
Figure 4:
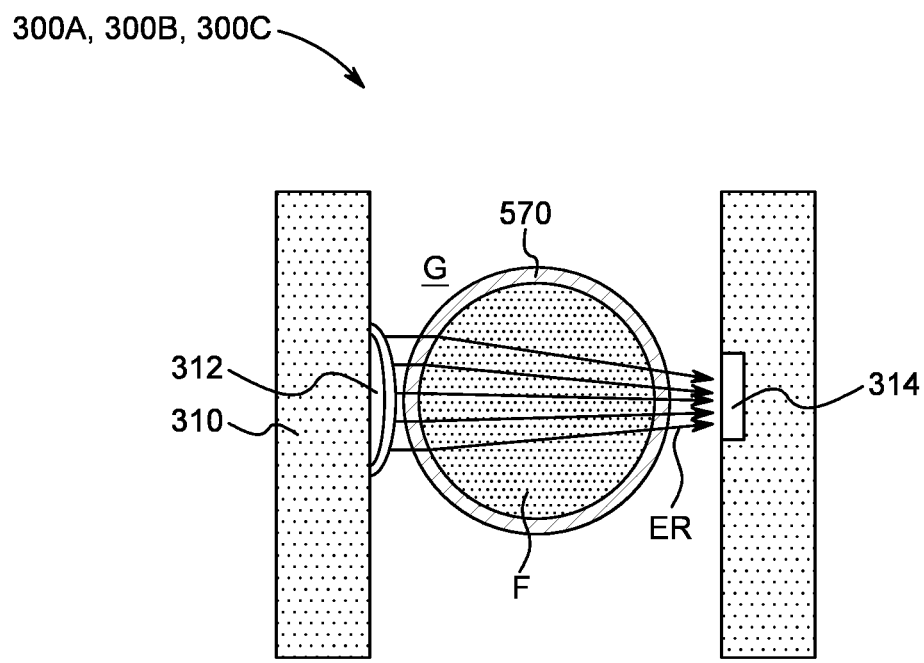
FIG. 4 is a front cross-sectional view of the sensor module of FIG. 3 associated with a liquid-filled fluid path section.
Figure 5:
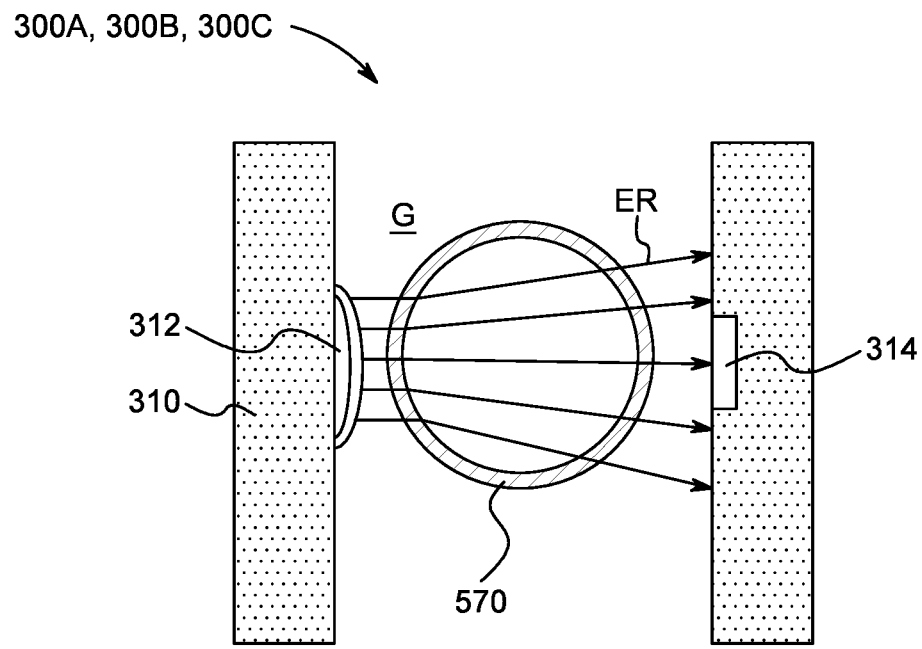
FIG. 5 is a front cross-sectional view of the sensor module of FIG. 3

Referring to FIG. 3-5, in some embodiments, each sensor module 300A, 300B. 300C may include one or more sensors 310 each including an emitter 312 and a collector or detector 314 as illustrated in FIG. 3. The emitter 312 and the detector 314 are spaced apart from one another defining a gap G in which is positioned the operatively associated fluid path section 570). The emitter 312 is configured to emit electromagnetic radiation ER (e.g. light) at a predetermined wavelength toward the detector 314. The electromagnetic radiation ER must pass through the fluid path section 570 to reach the detector 314. The fluid in the fluid path section 570) and, in some embodiments, the structure of the fluid path section 570) itself, absorbs and/or refracts some amount of the electromagnetic radiation ER generated by the emitter 312, and thus prevents that amount of electromagnetic radiation ER from reaching the detector 314. In addition, the contents of the fluid path section 570 and, in some embodiments, the structure of the fluid path section 570 itself, causes the electromagnetic radiation ER to diverge or converge before reaching the detector 314 due to the refraction index of the fluid and the fluid path section 570. Difference in measured absorption and/or refraction may be used to differentiate between an empty sensor 310 compared to one in which fluid path section 570 has been operatively inserted into the field of the sensor 310, where fluid path section 570 only contains air. In certain embodiments, the signal from sensor 310 may further indicate whether the fluid path section 570 has been properly inserted into the sensor 310. Once the fluid path section 570 is correctly installed within the sensor module 300A, 300B, 300C, sensor module 300A, 300B, 300C may then use differences in measured refraction to determine whether fluid path section 570) contains a liquid fluid (contrast or aqueous flushing fluid) or air.

In some embodiments, the emitter 312 may be one or more light emitting diodes (LEDs) or liquid crystal configured to emit electromagnetic radiation ER at a predetermined wavelength (or range of wavelengths), although other emitter light sources are within the scope of the present disclosure. In certain embodiments, the emitter 312 may be able to emit electromagnetic radiation ER at more than one wavelength, depending on the fluid to be measured. For example, the emitter 312 may be configured to emit light at a first wavelength and emit light a second or other wavelength depending on the requirements of the fluid injection procedure. The detector 314 may be any detector capable of converting a quantity of received light into an electrical signal, for example a phototransistor, photoresistor, or a photodiode. In various embodiments, the detector 314 may be configured to measure an amount of received electromagnetic radiation ER at different specific wavelengths, depending on the wavelength emitted by the emitter 312. The controller 900 may be configured to control the wavelength of light emitted by the emitter 312 and detected by the detector 314. In some embodiments, the emitter 312 is configured to emit electromagnetic radiation on the infrared (IR) spectrum, for example between about 700 nanometers (nm) and about 2000 nm. In some embodiments, the emitter 312 is configured to emit electromagnetic radiation on the ultraviolet (UV) spectrum, for example between about 10 nm and about 400 nm. In particular embodiments, the electromagnetic radiation emitted by the emitter 312 may have a wavelength from about 700 nm to about 2000 nm, in some embodiments from about 1440 nm to about 1460 nm, and in specific embodiments of about 1450 nm. In other embodiments, the electromagnetic radiation emitted by the emitter 312 may have a wavelength within the IR spectrum from about 750) nm to about 950 nm, or in another embodiment from about 800 nm to about 900 nm, in some embodiments from about 880 nm to about 900 nm, and in specific embodiments about 890 nm. In other embodiments, the electromagnetic radiation emitted by the emitter 312 may have a wavelength within the UV spectrum from about 300 nm to about 400 nm, or in another embodiment from about 350 nm to about 400 nm, in some embodiments from about 390 nm to about 400 nm, and in specific embodiments about 395 nm. In some embodiments, the emitter 312 may be configured to emit acoustic, e.g. ultrasonic, energy, and the detector 314 may be configured to detect acoustic energy. Electromagnetic radiation in the aforementioned wavelengths (e.g. IR and UV wavelengths) may have an advantage over other imaging protocols, such as ultrasound, in that electromagnetic radiation does not require acoustic coupling (e.g. compressive contact) between the fluid path section 570) and sensor 310.

The specific wavelength of electromagnetic radiation may be selected based on the fluids F used in the injection procedure and the structural properties of the fluid path section 570). Particularly, the wavelength(s) of electromagnetic radiation may be chosen that provide maximum differentiation in the output signal of the detector 314 for various fluids of concern. For example, the emitter 312 may be selected and/or configured to emit electromagnetic radiation of a wavelength that exhibits the greatest difference in transmission through saline and contrast media. In some embodiments, the emitter 312 may be configured to emit electromagnetic radiation at multiple wavelengths (either concurrently or in alternating pulses) to improve sensitivity of the sensor 310. For example, the emitter 312 may be configured to emit electromagnetic radiation at a first wavelength optimized for differentiating between saline and contrast media, and to emit electromagnetic radiation at a second wavelength optimized for differentiating between concentrations of contrast media.

In some embodiments, the wavelength(s) of electromagnetic radiation may be chosen to minimize adverse effects of factors on sensor performance, such as alignment of the electromagnetic radiation emitter 312 and detector 314, alignment of fluid path set 570) with the emitter 312 and detector 314: the material and geometry of the outer sidewall of fluid path section 570; and exposure of detector 314 to ambient light. The span of the gap G between the emitter 312 and detector 314 may also be selected to maximize differentiation in the output signal of detector 314 for various fluids. For example, empirical testing on a standard tube having a nominal outer diameter of 0.188 inches found that a gap G of 0.228 inches was preferable to gaps G of 0.188 inches and 0.208 inches in terms of the ability of detector 314 to differentiate between air, contrast, and saline in the tubing. (see FIGS. 8A and 8B)

FIG. 3 illustrates the absence of a fluid path section in the gap G, so the electromagnetic radiation ER must pass through only the air in the gap G to reach the detector 314. FIG. 4 illustrates the fluid path section 570 placed in the gap G in operative association with the sensor 310. The fluid path section 570 in FIG. 4 is filled with the injection fluid F as would be expected during a filling operation of an injection procedure where fluid is moved from the bulk fluid container 19A, 19B to the syringe 10A, 10B. The refractive index of the injection fluid F may cause the electromagnetic radiation ER passing through the fluid path section 570 to converge before reaching the detector 314, thereby causing an increase in signal intensity received and measured by the detector 314. Additionally, the injection fluid F (for example solute molecules dissolved in an aqueous solution, typical of saline flushing fluid or an imaging contrast) absorbs some of the electromagnetic radiation ER generated by the emitter 312, preventing some of the electromagnetic radiation ER from reaching the detector 314. FIG. 5 illustrates the fluid path section 570 placed in the gap G in operative association with the sensor 310, where the fluid path section 570 is filled with air as would be expected prior to priming the fluid path section 570 or initiating a filling operation of the syringe 10A, 10B, or which may occur if an air bubble is present in the injection fluid F during an injection procedure. The refractive index of the air causes the electromagnetic radiation ER passing through the fluid path section 570 to diverge before reaching the detector 314, thereby causing a decrease in signal intensity receive and measured by the detector 314.

Further, the absorption associated with the air-filled fluid path section 570 would absorb less light than a liquid filled fluid path section 570 (FIG. 4) but would absorb more light than in a situation where the fluid path section 570 is not in gap G (FIG. 3) due to the absorption of light by the polymeric material of the fluid path section sidewalls. In specific embodiments, light absorption by the content between the emitter 312 and detector 314 may cause a difference in signal intensity measured by the detector 314. For example, in FIG. 3, where no fluid path section 570 is present, the light may pass freely from the emitter 312 to the detector 314 of the sensor 310 with only a minimum decrease in signal intensity, since air has only a minimal absorption of light from the emitter 312 (which can be factored into any calculation). When a fluid filled fluid path section 570 is inserted into sensor 310, the signal of light passing from the emitter 312 to detector 314 is attenuated by absorption by the molecular makeup of the sidewalls of as well as the fluid within the fluid path section 570. In conditions where fluid path section 570 is filled with air, the signal of light passing from the emitter 312 to detector 314 is attenuated by absorption by the molecular makeup of the sidewalls of fluid path 570) (no absorption by the unprimed air in the fluid path or in a large air bubble). According to various embodiments, detector 312 may be able to use a difference in light attenuation resulting from different liquids within the fluid path to differentiate between different contrast types or concentrations; or between contrast and saline, within fluid path section 570).

The detector 314 is configured to transmit an output signal (e.g. an output voltage) to the controller 900 based on signal strength from the detected electromagnetic radiation ER. Thus, the output signal will be different depending on refractive index and absorption properties of the contents in the gap G, allowing the controller 900 to determine whether the fluid path section 570 is absent (FIG. 3), the fluid path section 570 is present and filled with medical fluid F (FIG. 4), or the fluid path section 570 is present and filled at least partially with air (FIG. 5). In various embodiments, the controller 900 may determine a type of fluid (e.g. from a known database of commercially available contrast media solution) and/or a dilution ratio of fluid (i.e. a ratio of contrast media to saline during a dual-flow injection) based on the output signal of the detector 314. In particular, the sensor module 300C (FIG. 2) downstream of the merge point of the patient lines 210A, 210B may be configured to measure dilution of the contrast from the first syringe 10A by saline from the second syringe 10B. To produce reliable results, the emitter 312, detector 314, and fluid path section 570 are selected and arranged so that the output signal generated by the detector 314 is sufficiently different between fluid types that the sensor 310 is able to distinguish between the different contrast agent types and/or the different dilution ratios. For example, if the sensor 310 is intended to distinguish between contrast media and saline, the emitter 312, detector 314, and fluid path section 570) are selected and arranged such that a range of output voltages of the detector 314 when saline is present in the fluid path section 570 does not overlap with a range of output voltages of the detector 314 when contrast media is present in the fluid path section 570. Similarly, if the sensor 310 is intended to distinguish between contrast media types, the emitter 312, detector 314, and fluid path section 570 are selected and arranged such that a range of output voltages of the detector 314 when a particular contrast type is present in the fluid path section 570) does not overlap with a range of output voltages of the detector 314 when a different contrast media type is present in the fluid path section 570.

Figure 23:
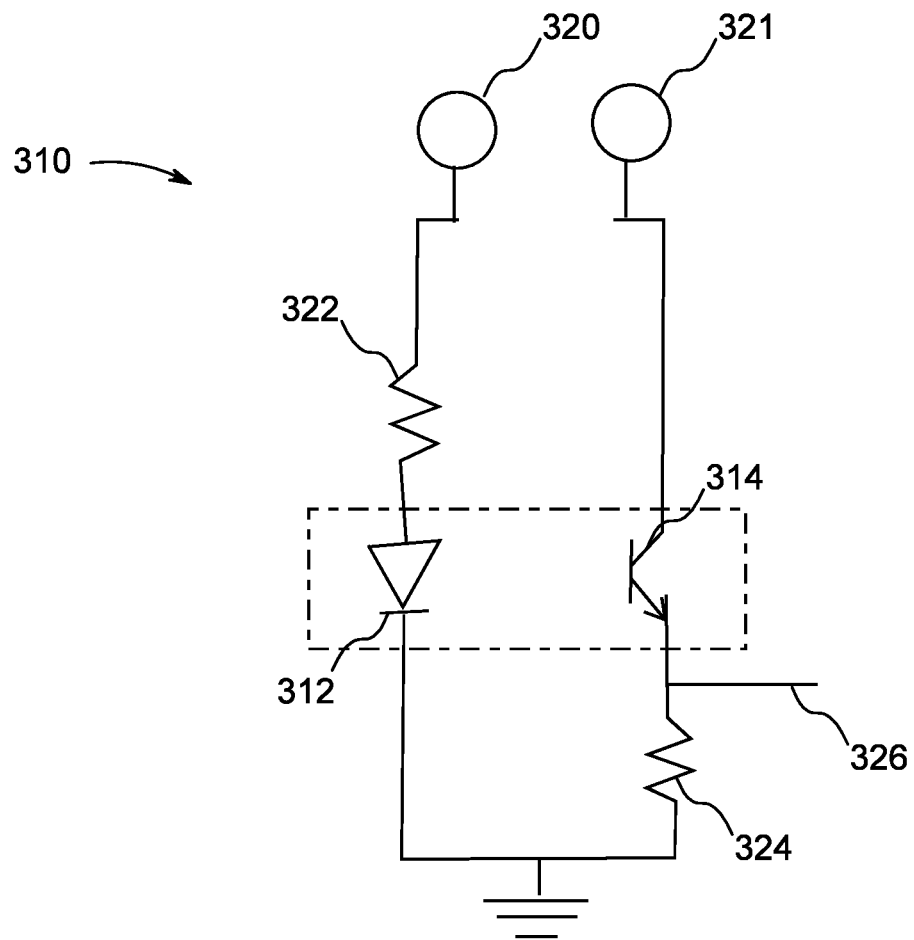
FIG. 23 is a circuit schematic of a sensor according to an embodiment of the present disclosure.

FIG. 23 illustrates an electrical schematic of the sensor 310 in accordance with an embodiment of the present disclosure. As noted herein, the sensor 310 includes the emitter 312 and the detector 314 arranged such that the detector 314 receives electromagnetic radiation from the emitter 312, with the received electromagnetic radiation being altered by the absorption and/or refraction of the fluid path section 570 and its contents. The emitter 312 and detector 314 are powered by respective power supplies 320, 321. The power supplies 320, 321 may be 5 volt power supplies, which may be standalone devices or outputs of the controller 900. The power supply 320 associated with the emitter 312 allows the controller 900 to calibrate the emitter 312 by adjusting supplied current. The power supply 321 supplies a fixed reference voltage to the detector 314 relating to the stability of the resulting output voltage of the sensor 310. The emitter 312 may include one or more LEDs emitting one or more specific wavelengths of electromagnetic radiation, with a current-limiting resistor 322 placed in series to maintain an appropriate forward current through the LED(s). The detector 314 may be one or more phototransistors, photoresistors, or photodiodes with an associated sensor resistor 324. The sensor resistor 324 converts a current generated by the detector 314 in response to detecting electromagnetic radiation into an output voltage signal 326 to pass to the controller 900.

Figure 6:
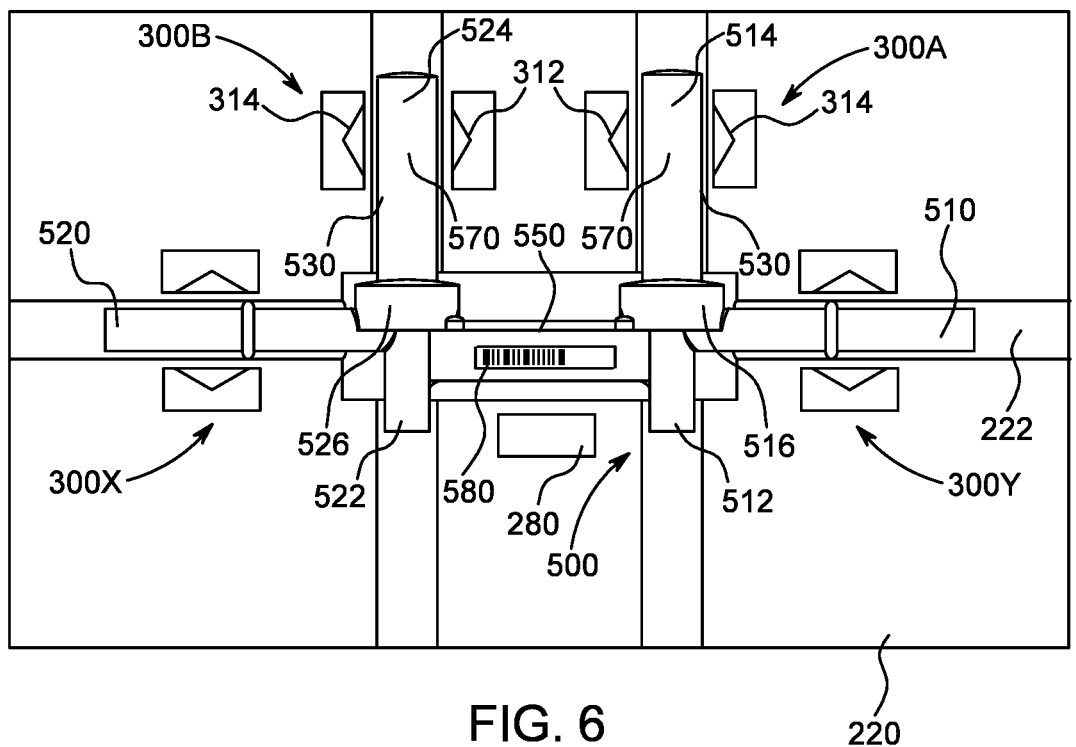
FIG. 6 is a front view of a manifold and manifold housing module according to an embodiment of the present disclosure.

Referring to FIG. 6, in some embodiments, sensor modules 300A, 300B may be provided in a manifold housing module 220 associated with fluid injector 12. The manifold housing module 220 may define a receiving channel 222 for removably receiving a manifold 500 of the fluid path set. The manifold 500 may be a disposable component serving as a junction for the first syringe line 208A, first patient line 210A, and first fill line 216A (FIG. 2). In particular, manifold 500 may include a first inlet port 510 connected to or integrally formed with syringe line 208A, a first outlet port 512 connected to or integrally formed with patient line 210A, and a first fill port 514 is connected to or integrally formed with fill line 216A. Similarly, manifold 500 may serve as a junction for the second syringe line 208B, second patient line 210B, and second fill line 216B (FIG. 2). The manifold 500 may include a second inlet port 520 connected to or integrally formed with syringe line 208B, a second outlet port 522 connected to or integrally formed with patient line 210B, and a second fill port 524 connected to or integrally formed with fill line 216B. The manifold 500 defines respective fluid path sections 570 adjacent to each of fill ports 514, 524 that are configured to be operatively positioned between the emitter 312 and detector 314 of respective sensor modules 300A, 300B.

The manifold 500 may include at least one connecting beam 550 that, along with the receiving channel 222, orients and positions the manifold 500 and correctly indexes and interfaces the fluid path sections 570 with the sensor modules 300A, 300B. Thus, the manifold 500 is designed to allow a user to quickly and accurately install the tubing set into the manifold housing module 220, such that the air detection regions of the fluid flow paths are correctly inserted into the reading portions of the sensor modules 300A, 300B. For example, in preparing the fluid injector system 2000 for a new injection procedure, the user may simply connect the syringe lines 208A, 208B to the syringes 10A, 10B, snap the manifold 500 into the manifold housing module 220, and connect the fill lines 216A, 216B to the bulk fluid sources 19A, 19B (for example by spiking the fill lines 216A, 216B into the respective bulk fluid source 19A, 19B) and the fluid path set should be ready for priming. In certain cases, the manifold 500 and the manifold housing module 220 may include complementary latching components, for example on the at least one connecting beam 550, to releasably engage the manifold 500 with the manifold housing module 220. In certain embodiments, the manifold 500 and associated fluid path components may be a disposable component configured for use during a single injection procedure or for a series of injection procedures on a single patient. In other embodiments, the manifold 500 and associated fluid path components may be a disposable component of a multi-use portion of the fluid path set, which can be used in conjunction with multiple single-use portions, over several fluid injection procedures before being disposed of, for example after a set number of injections or 24 hours of use.

The fluid path sections 570 each include a sidewall 530 configured to allow passage of electromagnetic radiation from the emitters 312 to the detectors 314 when the fluid path sections 570) are disposed in operative association with the sensor modules 300A, 300B. Each sidewall 530 is at least partially transparent to the predetermined wavelengths of electromagnetic radiation ER generated by the emitters 312. The sidewalls 530 may be made of an at least partially transparent material, such as a polymer, glass, transparent composite, crystal, or other suitable material. In certain embodiments, the sidewall 530 may be constructed of a plastic material such as polyethylene terephthalate (PET), polycarbonate (PC), or polypropylene (PP) having a predetermined index of refraction. In some embodiments, the index of refraction of the sidewall 530 is closer to an index of refraction of water than to an index of refraction of air. In some embodiments, the sidewall 530 may be rigid so that the sidewall 530 cannot deflect, which could alter the path of electromagnetic radiation ER through the fluid path section 570) and cause unreliable sensor readings. In certain embodiments, the sidewall 530 may be curved extending circumferentially around the outer surface of the fluid path section 570. In other embodiments, the sidewall 530 may have one or more substantially planar exterior surfaces and interior surfaces. The one or more substantially planar surfaces may be located so that the path of electromagnetic radiation from the emitter 312 to the detector 314 passes through the one or more substantially planar surfaces. According to these embodiments, the one or more substantially planar surfaces may minimize or eliminate any focusing or defocusing lensing effect by the surface on the beam of electromagnetic radiation as it passes through the first fluid path section 570. In other embodiments, sidewall 530 may include or act as a lens to concentrate or disperse the electromagnetic radiation passing through the fluid path section 570). For example, sidewall 530 may have one or more flat surfaces, which may more predictably transmit light than curved surfaces, and in some embodiments, sidewall 530) may be a square tube. In some embodiments, sidewall 530 may have a surface finish to concentrate or disperse electromagnetic radiation passing through fluid path section 570.

With reference to FIG. 6, manifold 500 may include one or more check valves, such as check valves 516, 526 respectively located in the fill ports 514, 524. Check valves 516, 526 may act to prevent backflow of fluid into the bulk fluid containers 19A, 19B during a pressurized injection. In some embodiments, additional check valves or actively-controlled valves (e.g. stopcocks, pinch valves, etc.) may be located in any of inlet ports 510, 520, outlet ports 512, 522, and fill ports 514, 524 to selectively control fluid flow through manifold 500.

The manifold 500 may include one or more encoded identifiers 580, such as a barcode, QR-code, RFID tag or the like, for example located on the at least one connecting beam 550) or fluid path wall. The fluid injector 12 may have an appropriately positioned reader 280, such as a barcode reader, QR-code reader, RFID reader, associated with the manifold housing module 220. Upon correct engagement of the manifold 500 with the manifold housing module 220, the encoded identifier 580 is read by the reader to determine one or more property of the manifold 500 and associated fluid path elements, such as at least one of: that the manifold 500 is correctly inserted, that the correct manifold 500 for the injection procedure, that the manufacture date of the manifold 500 and associated fluid path components is within the required time frame, and to determine whether the manufacturer of the manifold 500 is an approved manufacturer. If the controller 900 determines that the encoded identifier indicated that there may be an issue with the manifold 500, the controller 900 may alert the user and require correction of the issue before the fluid injection procedure may be performed.

With continued reference to FIG. 6, the manifold housing module 220 may include additional sensor modules 300X, 300Y associated with the fluid path sections adjacent the respective inlet port 510, 520. The additional sensor modules 300X, 300Y may generally be similar in structure to the sensor modules 300A, 300B. However, various attributes of the additional sensor modules 300X, 300Y may differ from the sensor modules 300A, 300B in order to facilitate different functions. For example, the additional sensor modules 300X, 300Y may be particularly configured for air bubble detection and analysis, as described in PCT International Application PCT/US2022/017812, filed 25 Feb. 2022, the disclosures of each of which are incorporated herein by this reference. Further details of the structure and function of the manifold 500 and the manifold housing module 220 are shown in PCT International Application PCT/US2022/017812.

Figure 7:
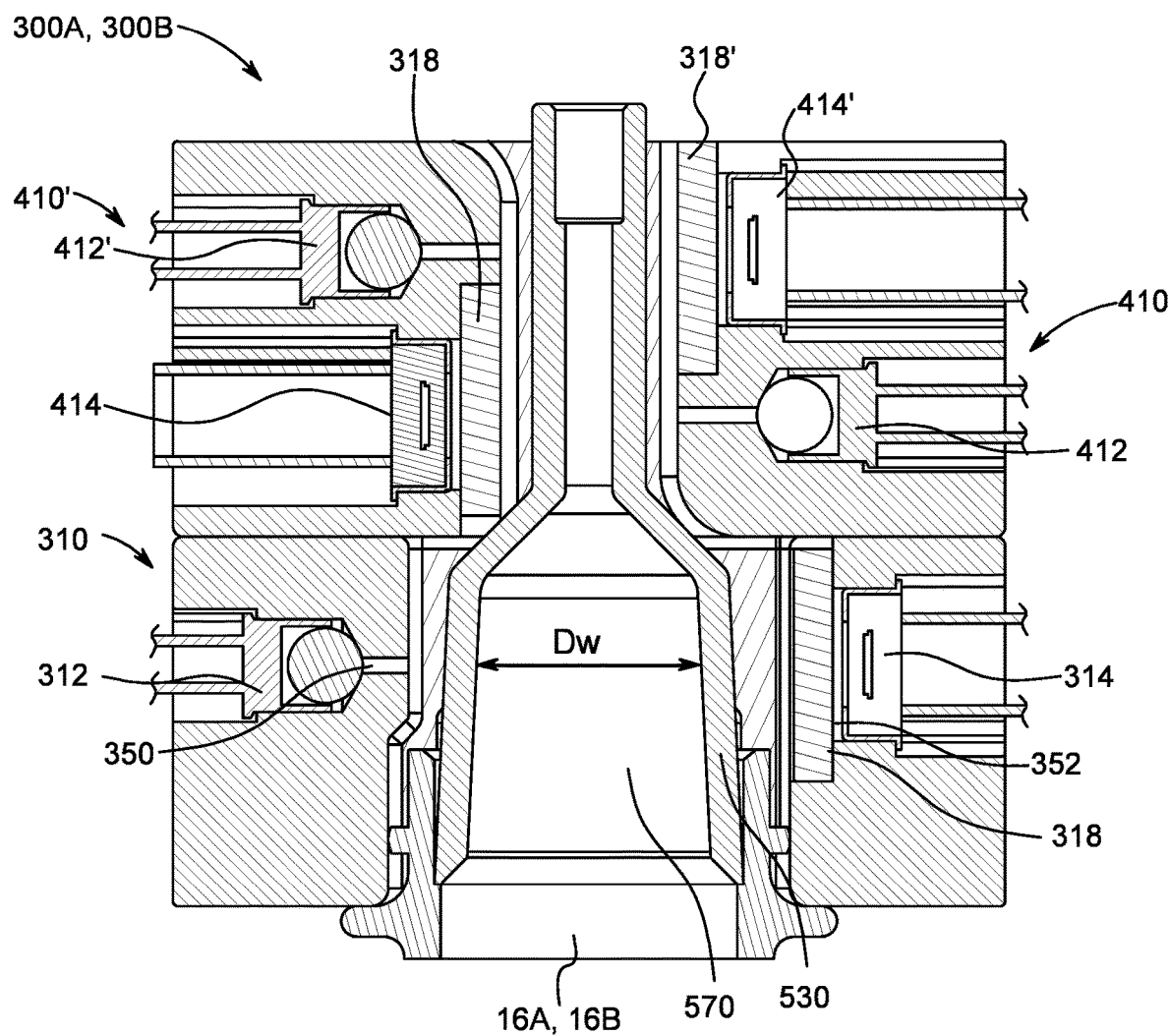
FIG. 7 is a side cross-sectional view of a syringe tip, fluid path section, and a sensor module according to an embodiment of the present disclosure.

Referring to FIG. 7, one embodiment of sensor modules 300A, 300B is illustrated in operative association with a corresponding syringe tip 16A, 16B so as to detect fluid in the fluid path section 570 entering the corresponding syringe 10A, 10B during a filling operation. The syringe tips 16A, 16B themselves may serve as fluid path sections aligned with the sensor 310, or a separate fluid path section 570 may be attached to the syringe tips 16A, 16B and aligned with the sensor 310. The fluid path section 570 includes a sidewall 530, which may be similar to the sidewall described in connection with FIG. 6, that is at least partially transparent to the wavelength of electromagnetic radiation generated by the emitter 312. The sidewall 530 may be constructed of a plastic material such as polyethylene terephthalate (PET), polycarbonate (PC), or polypropylene (PP) having a predetermined index of refraction. In some embodiments, the index of refraction of the sidewall 530 is closer to an index of refraction of water than to an index of refraction of air. In some embodiments, the sidewall 530 may be rigid so that the sidewall 530 cannot deflect, which could alter the path of electromagnetic radiation ER through the fluid path section 570) and cause unreliable sensor readings. In some embodiments, the sidewall 530 may include or act as a lens to refract and concentrate or disperse the electromagnetic radiation passing through the fluid path section 570. In some embodiments, the sidewall 530 may have a surface finish to concentrate or disperse the electromagnetic radiation passing through the fluid path section 570. The sensor modules 300A, 300B may be free to rotate about the syringe tips 16A, 16B to allow the operator freedom in positioning the sensor modules 300A, 300B, e.g., to avoid particular orientations that would receive large amounts of ambient light. Optic filters 318 may be provided between the emitter 312 and detector 314 to prevent ambient light from affecting a measurement of detector 314.

The emitter 312 and the detector 314 may be arranged in a wide diameter section Dw of the fluid path section 570. This arrangement forces the electromagnetic radiation emitted by the emitter 312 to travel through a relatively large diameter of fluid, allowing for more absorption and/or refraction of the electromagnetic radiation by the fluid. Empirical testing has shown that the greater absorption allowed by larger diameter of fluid increases the differentiation in detector output signal between fluid types. Thus, an increase in the diameter of the fluid path section 570 through which the electromagnetic radiation travels can lead to more reliable and improved determinations of the fluid properties within the fluid path section 570) by the controller 900. In some empirically tested embodiments, increasing diameter of the fluid path section 570) accentuates the difference in absorption in a squared relationship: i.e., a small increase in diameter of the fluid path section has a relatively larger impact on a fluid's absorption of electromagnetic radiation.

The sensor modules 300A, 300B may include a collimating aperture 350 associated with the emitter 312 and/or a collimating aperture 352 associated the detector 314. The collimating aperture 350) associated with the emitter 312 may restrict the electromagnetic radiation leaving the emitter 312 to a substantially straight trajectory toward the detector 314. The collimating aperture 352 associated with the detector 314 may limit the peripheral field of view of the detector 314 such that only electromagnetic radiation coming from the direction of the emitter 312 can reach the detectors 314. Thus, the collimating aperture 352 may shield the detector 314 from ambient light sources. In some embodiments, the collimating apertures 350, 352 may have a lesser length than diameter. In some embodiments, the collimating apertures 350, 352 may have a greater length than diameter.

The sensor modules 300A, 300B may include one or more additional sensors 410, 410' configured to provide further analysis of the fluid path section 570. The additional sensors 410, 410' may generally be similar in structure to the sensor 310, so any features of the sensor 310 described herein may equally apply to the additional sensors 410, 410'. However, various attributes of the additional sensors 410, 410' may differ from the sensor 310 in order to facilitate different functions. For example, the additional sensors 410, 410' may be particularly configured for air bubble detection and analysis. Examples of additional sensors for determination of air bubble detection and analysis are presented in PCT International Application PCT/US2022/017812. Respective emitters 412, 412' of the additional sensors 410, 410' may be configured to emit electromagnetic radiation at the same or a different wavelength than the sensor 310. In the embodiment shown in FIG. 7, the additional sensors 410, 410' are located downstream of the sensor 310. In other embodiments, the additional sensors 410, 410' may be located upstream of the sensor 310, or at an entirely different location in the fluid path set. The sensor 310 and the additional sensors 410, 410' may be configured to differentiate between air and fluid (e.g., saline and contrast media) in the fluid path section 570. In some embodiments, the additional sensors 410, 410' may be configured to work in tandem with the controller 900 to detect air bubbles in the fluid path section 570, to determine the flow rate of detected air bubbles, and/or to determine the volume of detected air bubbles. Controller 900 may be configured to determine a flow rate of such detected air bubbles based on a time offset between the air bubbles being detected by the proximal detector 414 and distal detector 414'.

Figure 24:
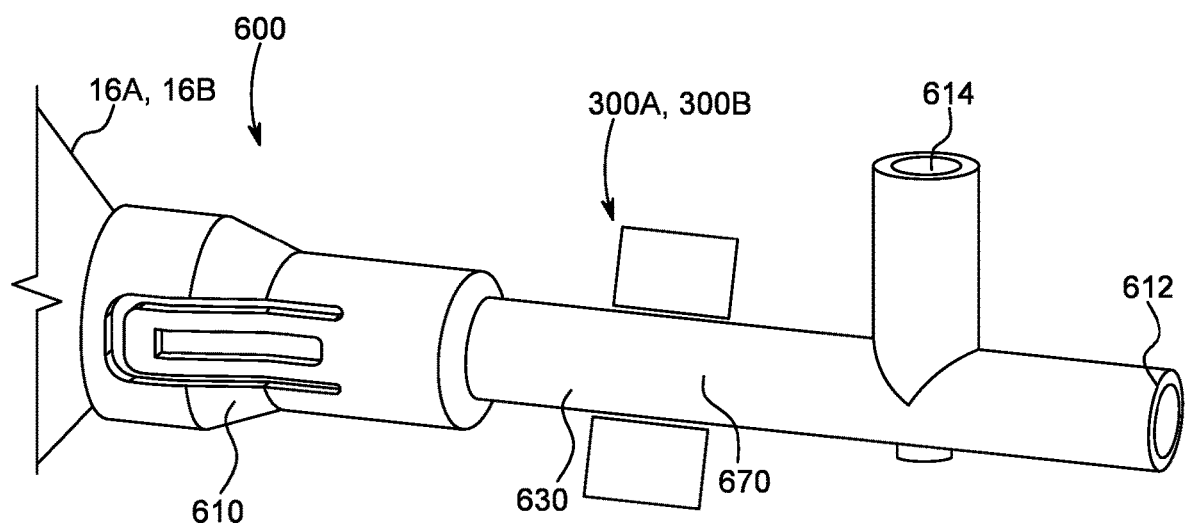
FIG. 24 is a perspective view of a syringe tip, manifold, and sensor module according to an embodiment of the present disclosure.

Referring to FIG. 24, in another embodiment, a manifold 600 including a fluid path section 670 may be attached to each syringe tip 16A, 16B, and the sensor modules 300A, 300B may be placed in operative association with the fluid path section 670 of the manifold 600. The manifold 600 and associated sidewall 630 may clip to or otherwise engage with corresponding features of on the tip 16A, 16B of syringes 10A, 10B by a clipping engagement mechanism as described in PCT International Application No. PCT/US2021/018523, the disclosure of which is incorporated by this reference. The manifold 600 includes an inlet port 610 configured for connection to the syringe tip 16A, 16B with or without (as shown) intervening flexible tubing (i.e. the corresponding syringe line 208A, 208B). The manifold 600 further includes an outlet port 612 configured for connection to the corresponding patient line 210A, 210B, and a fill port 614 configured for connection to the corresponding fill line 216A, 216B. The fluid path section 670 includes a sidewall 630, which may be substantially similar to the sidewall 530 shown and described in connection with FIGS. 6 and 7.

Referring to FIGS. 1, 2, 6, 7, and 24, in certain embodiments, the sensor modules 300A, 300B may be utilized for gross air detection within the fill lines 216A, 216B during an angiography (CV) or computed tomography (CT) procedure that accommodates refill of the syringes 10A, 10B during use from a bulk fluid containers 19A, 19B. As noted herein, the sensor modules 300A, 300B may be used to distinguish between injection fluid F and air in the fluid path section 570, to distinguish between two types of injection fluid common to the MR. CV or CT injection procedures (i.e., contrast types and saline), to distinguish between type and/or concentration of contrast media, to determine if the fluid path section 570 has been inserted into the sensor module 300A, 300B, and to determine the presence or absence of the fluid path section 570 itself. In particular, the controller 900 may be configured to automatically identify the fluid content of each syringe 10A, 10B based on the output signal of the detector 314. The controller 900 may display the contents of the syringes 10A, 10B to the operator, for example via a message or graphic on the GUI 11 or by a color associated with the fluid type (e.g., green or purple for contrast and blue for saline or other flushing solution). For example, the GUI 11 may graphically depict the syringes 10A, 10B, showing each in a predetermined color depending on the contents of the syringes 10A, 10B. Presuming the syringes 10A, 10B are filled as expected, with the first syringe 10A containing contrast media and the second syringe 10B containing saline, the GUI 11 could illustrate the first syringe 10A in green or purple and the second syringe 10B in blue. It is understood that other colors may be used to represent certain fluid types and represent when air is detected the sensor modules 300A, 300B.

In some embodiments, the controller 900 may illuminate the syringes 10A, 10B or other portions of the system 2000 to indicate the contents of the syringes 10A, 10B as determined by the sensor modules 300A, 300B and the controller 900. For example, the controller 900 may illuminate a light source optically connected to each syringe 10A, 10B, with the syringes 10A, 10B acting as light tubes to display a color indicative of the fill contents of the syringes 10A, 10B (e.g. green for contrast media and blue for saline). The plungers 14A, 14B may be backlit as described in U.S. Application Publication No. 2017/0056603, the disclosure of which is hereby incorporated by reference in its entirety, to indicate the contents of the syringes 10A, 10B as determined by sensor modules 300A, 300B.

In some embodiments, the controller 900 may be configured to communicate a warning to the operator, for example on the GUI 11 or in the form of a warning alert (e.g., audible or visual), if there is an error in the fluid arrangement vis-à-vis the requirements of a prescribed injection protocol. In some embodiments, the controller 900 may utilize a visual indication, for example a light display to indicate the absence of the fluid path section 570 in operative position in the sensor modules 300A, 300B (e.g., yellow warning light), the presence of air in the fluid path section 570 (e.g., red stop injection light), the presence of saline in the fluid path section 570) (blue light), or the presence of contrast media in the fluid path section 570) (e.g., green light). In certain embodiments, if air is detected in the fluid path section 570, the controller 900 may be configured to disable the injection procedure until a purging operation is performed and no further air is detected in the tubing, either automatically by the controller 900 or under direction of the operator.

In some embodiments, the controller 900 may be configured to perform safety checks and/or adjust parameters of an injection procedure if a fault is detected prior to or during an injection. For example, the controller 900, via the sensor module 300A associated with the first syringe 10A, may monitor the fluid path section 570 during a filling operation in which contrast media is drawn from the bulk fluid container 19A into the syringe 10A. The controller 900 may monitor the output signal of the detector 314 of the sensor module 300A to determine whether first syringe 10A is indeed receiving contrast media or is instead being filled with saline—for example because the operator incorrectly connected the bulk fluid containers 19A, 19B to the wrong syringes 10A, 10B. Similarly, the controller 900 may monitor the output signal of the detector 314 of the sensor module 300B to determine whether the second syringe 10B intended to be filled with saline is instead being filled with contrast media. If either or both conditions are true, the controller 900 can alert the operator, via a message displayed on the GUI 11, and/or automatically stop the fill procedure. In some embodiments, the controller 900 is configured to continue with the fill procedure and adjust the injection protocol and GUI display so that the first syringe 10A is shown as the saline syringe (i.e., by highlighting the syringe blue on the GUI) and the controller injects the saline from syringe 10A using parameters that were programmed for saline and originally intended to be injected by the second syringe 10B. In a similar manner, the controller 900 may adjust the injection protocol and GUI display so that the second syringe 10A is shown as the contrast syringe (i.e., by highlighting the syringe green on the GUI) and the controller injects the contrast from syringe 10B using parameters that were programmed for the contrast injection and originally intended to be injected by the first syringe 10A. In such embodiments, the controller 900 may be configured to update the display of the GUI to indicate this reversal of which syringe delivers which medical fluid. The capability of proceeding with an injection procedure even if the syringes 10A, 10B are filled incorrectly can reduce waste as the improperly loaded injection fluids need not be discarded and the filling operation need not be repeated.

In some embodiments, the controller 900 may be configured to adjust an injection ratio of contrast media to saline if the sensor module 300A detects that the concentration of the contrast media in the first syringe 10A is different than the concentration required by the injection protocol. If the controller 900 determines, based on the output signal of the sensor module 300A, that the contrast media in the syringe 10A is more concentrated than prescribed in the injection protocol, the controller 900 can alert the operator and/or automatically increase the ratio of saline injected during the procedure to dilute the concentration of the contrast media delivered to the patient. Similarly, in a dual flow procedure the controller 900 can reduce the injection rate of saline during the injection procedure to increase the concentration of the contrast media, for example if the contrast media in the first syringe 10A is less concentrated than prescribed in the injection protocol.

According to various embodiments, when no fluid path section is present in one or both of the sensor modules 300A, 300B, the resulting output signal from the corresponding detector 314 may be used by the controller 900 as a calibration point against which the controller 900 can assess subsequent output signals from the detector 314. When the fluid path section 570) contains air or an air bubble, a lower level of light transmission occurs through the fluid path section, for example due to absorption or scattering of light by the sidewall 530, such that less light reaches the detector 314, resulting in a lower detector output voltage. Alternatively, when a fluid is present in the fluid path section 570, the fluid light adsorption properties and/or index of refraction causes the light to be absorbed and/or refract as it travels through the fluid path section 570, resulting in an even lower level of light reaching the detector 314 compared to air in the fluid path section 570. The type of fluid affects the light transmission properties. For example, saline absorbs/refracts a first amount of light to the detector 314 greater than the amount of light absorbed/refracted by an air filled fluid path section 570, due to the solute (salts) dissolved in the aqueous solution, resulting in a first voltage readout lower than for air or for the absence of the fluid path section 570. Contrast media absorbs/refracts a second amount of light to the detector 134 greater than the amount of light absorbed/refracted by a saline or air filled fluid path section 570 or no fluid path, due to the type of solute (contrast molecules) dissolved in the aqueous solution, resulting in a lower voltage readout. While the foregoing description associates increased light transmission with higher voltage outputs of detector 314 and greater light absorption with a lower voltage output, this relationship is a function of the actual circuitry driving sensor 310, such that some embodiments may exhibit a reduction in voltage output of the detector at higher light transmittance.

As described herein, according to certain embodiments the sensitivity of the detector 314 may also allow differentiation of different types of contrast and/or different concentrations of the same contrast media. For example, different concentrations of the same contrast media will have different densities due to different amounts of solute dissolved in the solution, resulting in different indexes of refraction and/or different amounts of light absorption. As such, the fluids will allow different levels of electromagnetic radiation to reach the detector 314, resulting in different detector output voltage signals. In some embodiments, the controller 900 may be calibrated or may be configured to reference a database associated with output voltages of different contrast types or different contrast concentrations, for example in a look-up database programmed into the controller 900. The controller 900 may thus be able to determine which brand, type, and/or concentration of contrast media is in the first syringe 10A (or in the second syringe 10B in the event that the second syringe 10B is inadvertently filled with contrast media) and update the GUI as necessary or alert the user that an incorrect contrast or an incorrect contrast concentration has been loaded into syringe 10A.

In some embodiments, the controller 900 may determine the type of fluid in the fluid path section in order to optimize fill time of the syringes 10A, 10B. By identifying the type of fluid in the fill fluid line 216A, 216B, the controller 900 may set a predetermined safe filling rate for the syringes 10A, 10B, i.e. a flow rate into the syringes 10A, 10B that minimizes the syringe fill time while reducing the occurrence of bubble generated in the fluid by excess flow rate of the fluid into the syringe. For example, the controller 900 may store and utilize the results of air detection and correlate them to specific fill speeds so that an optimal fill rate (fastest speed) may be determined that prevents or reduces introduction of air bubbles into the fluid in the syringes 10A, 10B. For example, a predetermined safe filling rate for saline may be higher than a predetermined safe filling rate of contrast media.

Figure 8A:
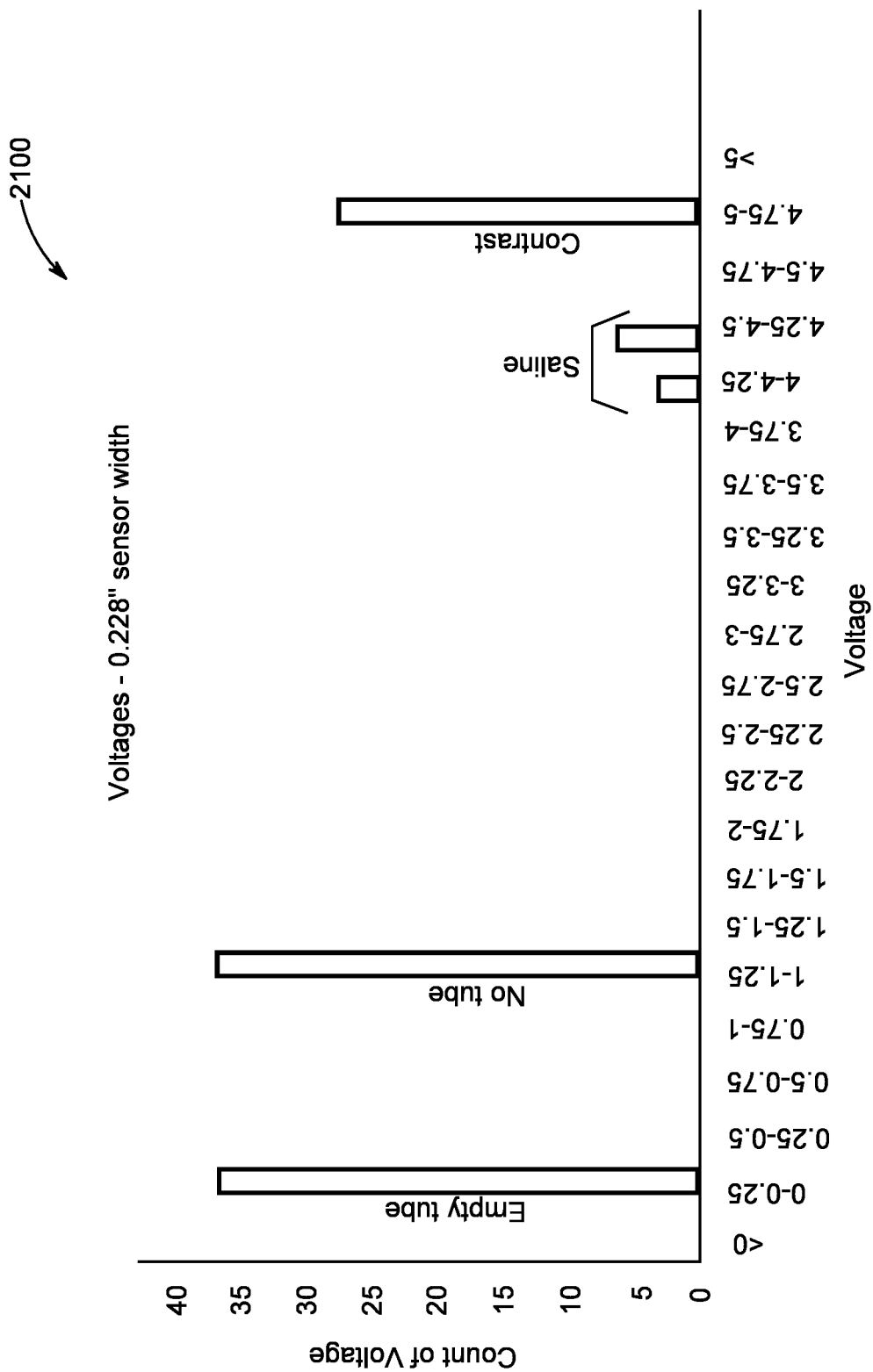
FIG. 8A is a histogram of sensor output voltage for various fluids in a fluid path section using infrared radiation, according to an embodiment of the present disclosure.

Referring to FIG. 8A, a histogram 2100 shows empirically observed output voltages of the detector 314 for various fluids in the fluid path section 570 operatively associated with the sensor 310. The wavelength of light according utilized in FIGS. 8A and 8B was 890 nm. The voltages were measured in 0.188 inch outer diameter tubing with infrared light generated by the emitter 312, and with a sensor gap G of 0.228 inches. The gap G of 0.228 inches was found to be the optimal size for obtaining signal differentiation in 0.188 inch tube. As may be appreciated from FIG. 8A, the observed output voltages of the detector 314 for an empty tube (i.e. only air in the fluid path section 570) fell within a range of 0) volts to 0.25 volts. The observed output voltages of the detector 314 for no tube (i.e. the fluid path section 570) not positioned in operative association with the sensor 310) fell within a range of 1 volt to 1.25 volts. The observed output voltages of the detector 314 for saline in the fluid path section fell in a range of 3.75 volts to 4.25 volts. And the observed output voltages of the detector 314 for contrast in the fluid path section 570) fell in a range of 4.75 volts to 5 volts. The clustering of voltage outputs exhibited by the various fluids (or lack thereof) in the fluid path section 570 illustrate that the sensor 310 may reliably differentiate between these fluid types based on the output voltage of the detector 314.

Figure 8B:
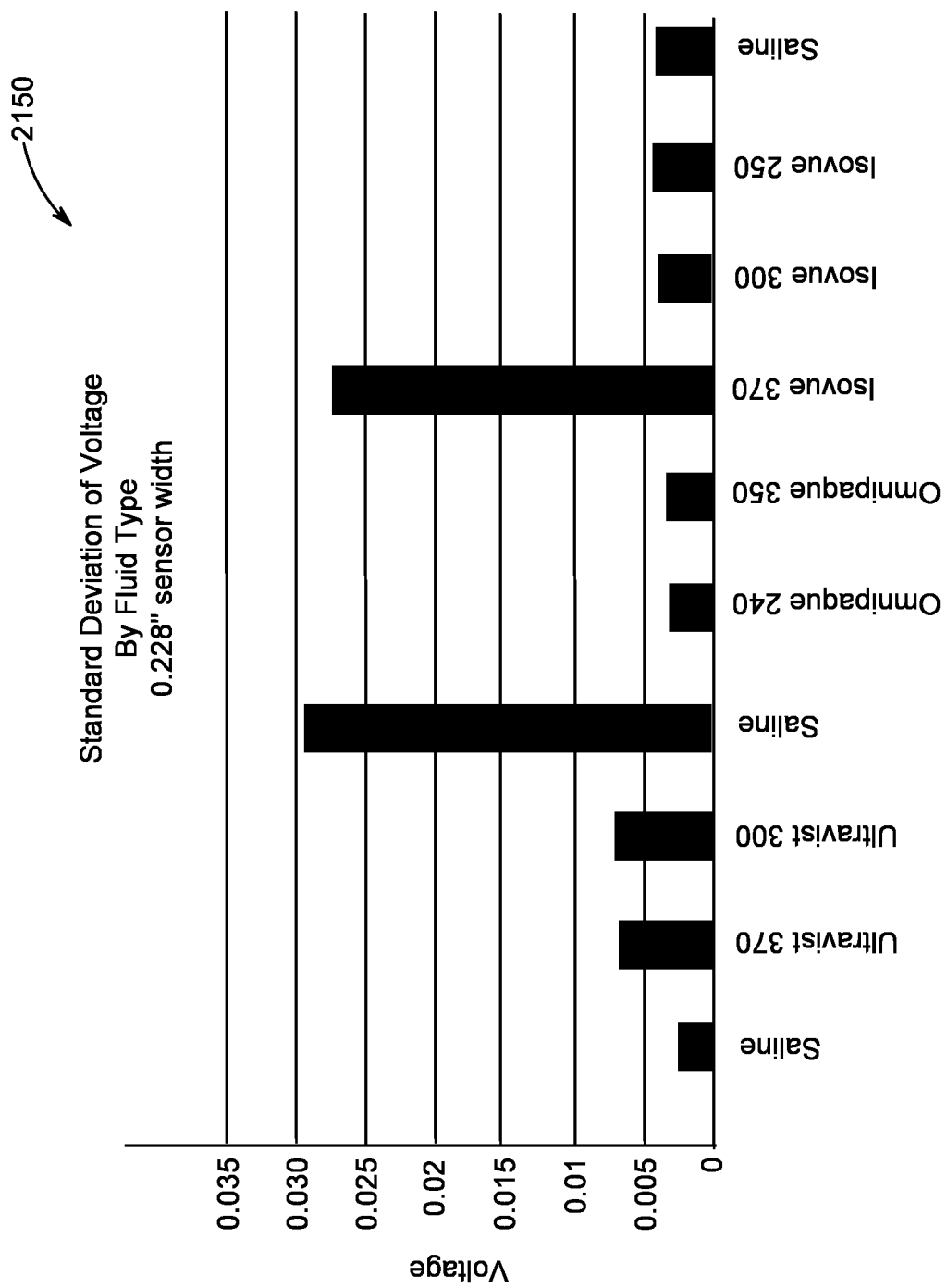
FIG. 8B is a plot of standard deviation of sensor output voltage from FIG. 8A for various types of contrast media in a fluid path section using infrared radiation.

Referring to FIG. 8B, a graph 2150 shows the standard deviation of detector output voltages over several test measurements of various fluids in the fluid path section 570, again using infrared light and a gap G of 0.228 inches as shown in FIG. 8A. The fluids for which data is shown include saline (for which three sets of data were analyzed) and the following commercially available contrast media solutions: Ultravist® 370, Ultravist® 300, Omnipaque™ 240, Omnipaque™ 350, Isovue® 370, Isovue® 300, and Isovue® 250. For all fluids except Isovue® 370 and one instance of saline, the standard deviation in the detector output voltages was less than 0.01 volts. The low standards of deviation for these fluids indicate that the output voltage of the detector 314 is consistent for each particular fluid, again indicating that the sensor 310 can reliably differentiate between contrast media solutions based on the detector output voltage. Based on this or similar empirical data, the controller 900 may be programmed with predetermined thresholds, such as upper bounds and lower bounds, associated with air, saline, and various types of contrast media. During an injection procedure, if the output signal from the detector 314 falls within the predetermined upper and lower bounds associated with air, the controller 900 determines that air is present in the fluid path section 570. Likewise, if the output signal from the detector falls within the predetermined upper and lower bounds associated with contrast media, the controller 900 determines that contrast media is present in the fluid path section 570. In some embodiments, only an upper bound or only a lower bound may be used as one of the predetermined thresholds. For example, the controller 900 may not have an upper bound associated with air, as the output voltage signal of saline or contrast media would never be less than that of air. In some embodiments, the controller 900 may interpret an output signal significantly outside an expected range of values as a fault condition and may alert the operator (for example via a message displayed on the GUI 11) and/or automatically halt the injection procedure. For example, if the output signal is above 5 volts in this embodiment, which as evident from graph 2100 is greater than the expected output voltage associated with any fluid in the fluid path section 570, the controller 900 may determine that a fault has occurred.

Figure 9:
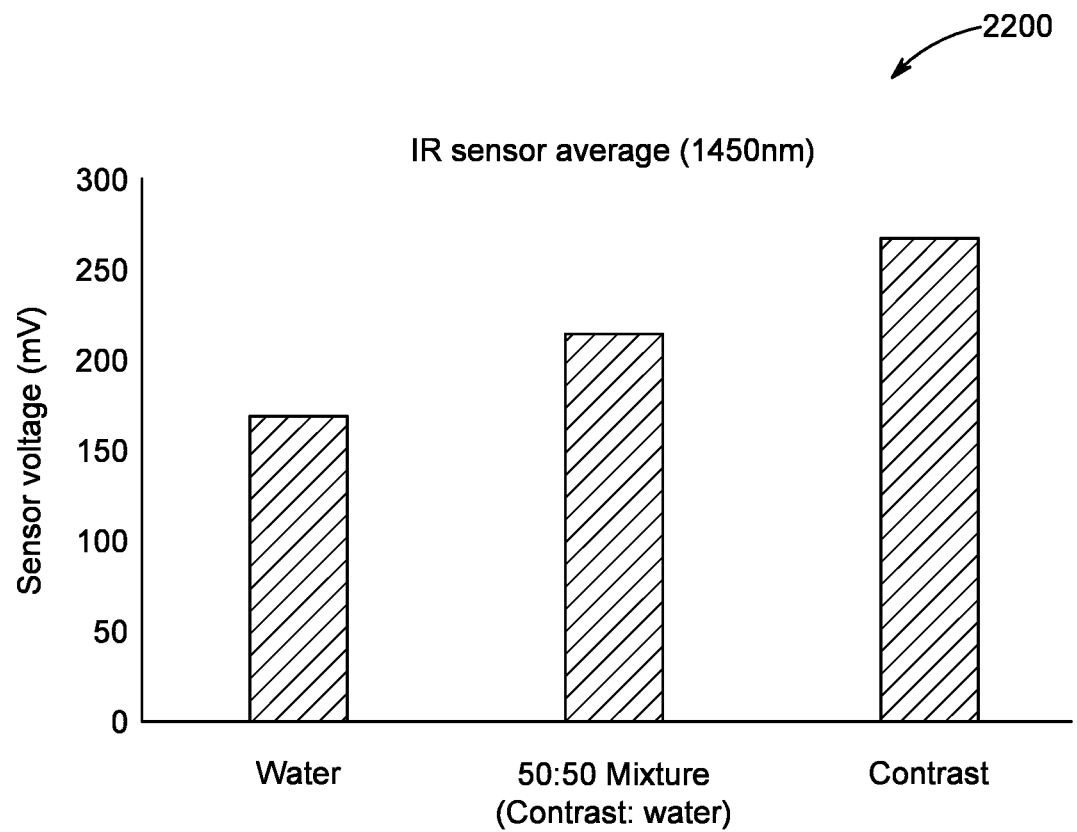
FIG. 9 is a graph of average sensor output voltage for various concentrations of contrast media in a fluid path section using infrared radiation, according to an embodiment of the present disclosure.

Referring to FIG. 9, graph 2200 shows empirically observed detector output signal voltages for water, contrast media, and a 50:50 solution of water and contrast media, again for the emitter 312 operating at 1450 nm. In this embodiment, the average detector output voltage for water in the fluid path section 570 is between 150 millivolt (mV) and 200 mV, the average detector output voltage for a 50:50 solution of contrast and water in the fluid path section 570) is between 200 mV and 250 mV, and the average detector output voltage for contrast media in the fluid path section 570) is between 250 mV and 300 mV.

Figure 10:
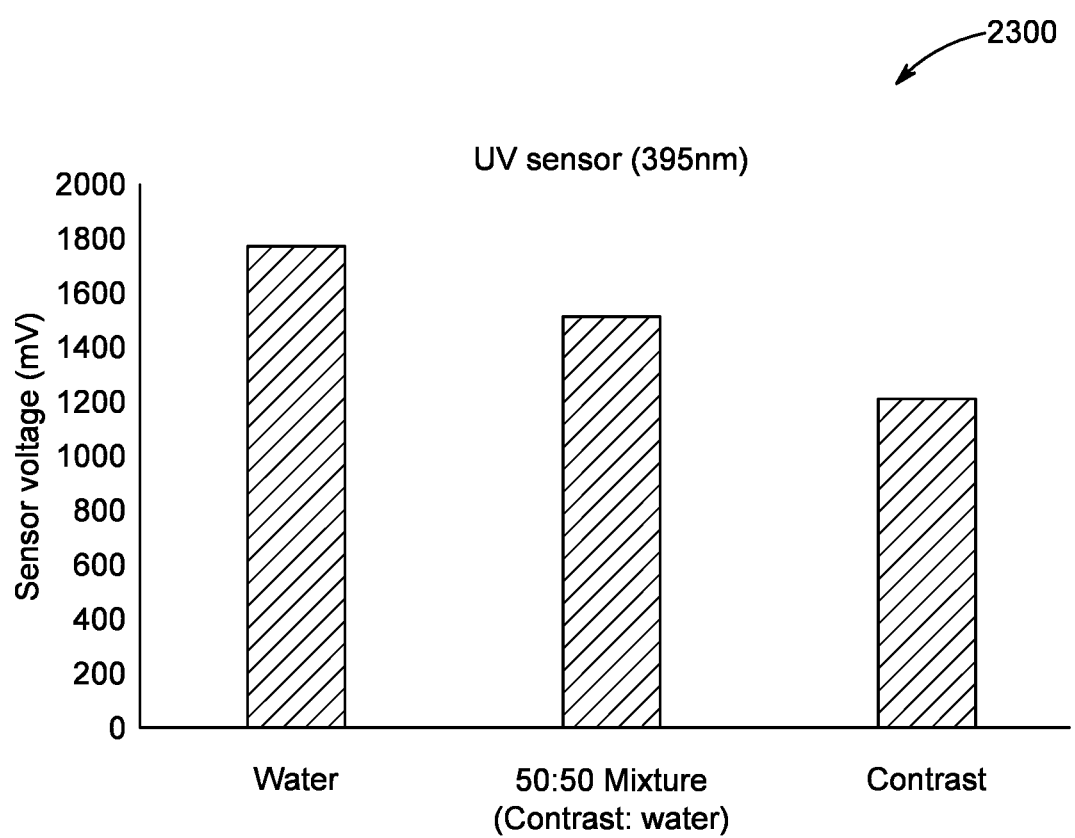
FIG. 10 is a graph of average sensor output voltage for various concentrations of contrast media in a fluid path section using ultraviolet radiation, according to an embodiment of the present disclosure.

Referring to FIG. 10, graph 2300 shows empirically observed detector output signal voltages for water, contrast media, and a 50:50 solution of water and contrast media, in an embodiment in which the emitter 312 generates electromagnetic radiation on the ultraviolet spectrum at 395 nm. In this embodiment, the average detector output voltage for water in the fluid path section 570 is between 1600 mV and 1800 mV, the average detector output voltage for a 50:50 solution of contrast media and water in the fluid path section 570 is between 1400 mV and 1600 mV, and the average detector output voltage for contrast media in the fluid path section 570 is approximately 1200 mV.

Figure 11:
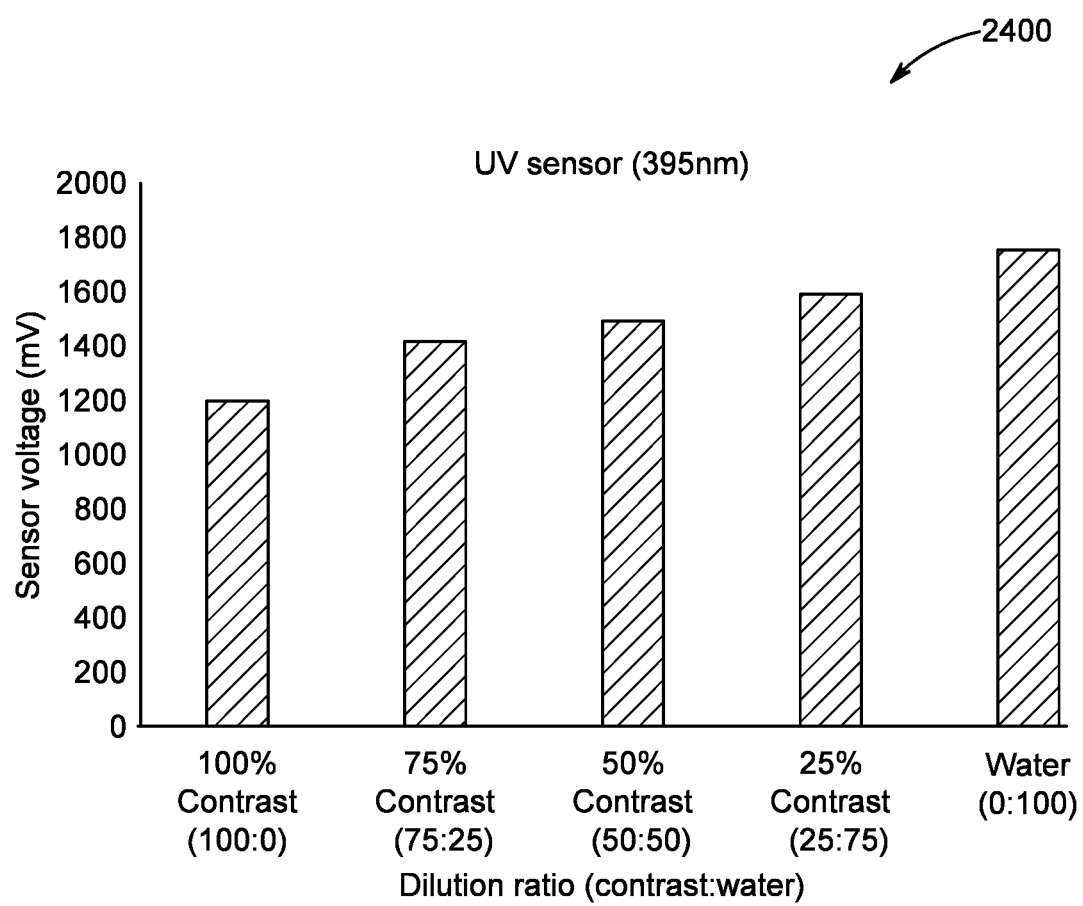
FIG. 11 is a graph of average sensor output voltage for various concentrations of contrast media in a fluid path section using ultraviolet radiation, according to an embodiment of the present disclosure.

Referring to FIG. 11, graph 2400 shows empirically observed detector output signal voltages for various dilution ratios of contrast media to water, again in an embodiment in which the emitter 312 generates electromagnetic radiation on the UV spectrum at about 395 nm. In this embodiment, the average detector output voltage for 100% contrast media in the fluid path section 570 is approximately 1200 mV, and the average detector output voltage gradually increases at 75% contrast. 50% contrast, 25% contrast, and 0% contrast (100% water). Thus, in this embodiment, the percentage of contrast media in the solution has an inverse effect on the output voltage of the detector 314.

FIGS. 8A-11 merely show data for a small number of embodiments, with specific configurations of the sensor 310. Other configurations, which may use a different type of emitter 312 or detector 314, different circuitry associated with the emitter 312 or detector 314, different gap spacing between the emitter 312 and the detector 314, different tubing diameters, different strengths of electromagnetic radiation, and/or different optical lenses or filters may produce different output voltages when detecting the same fluids as illustrated in FIGS. 8A-11. In some embodiments, for example, the detector 314 may output a voltage of approximately 1.609 volts if the fluid path section is not present, approximately 0.609 volts if the fluid path section is filled with air, approximately 3.43 volts if the fluid path section is filled with saline, and approximately 4.65 volts if the fluid path section is filled with contrast media. In other embodiments, the detector 314 may output a voltage of approximately 5.0 volts if the fluid path section is not present, approximately 2.5 volts if the fluid path section is filled with air, and approximately 1.0 volts if the fluid path section is filled with contrast media. Detector output voltages may be manipulated to a certain extent through calibration (e.g. changing the resistor 322, 324 in the sensor circuit of FIG. 23) to produce output voltages with greater sensitivity.

Figure 12:
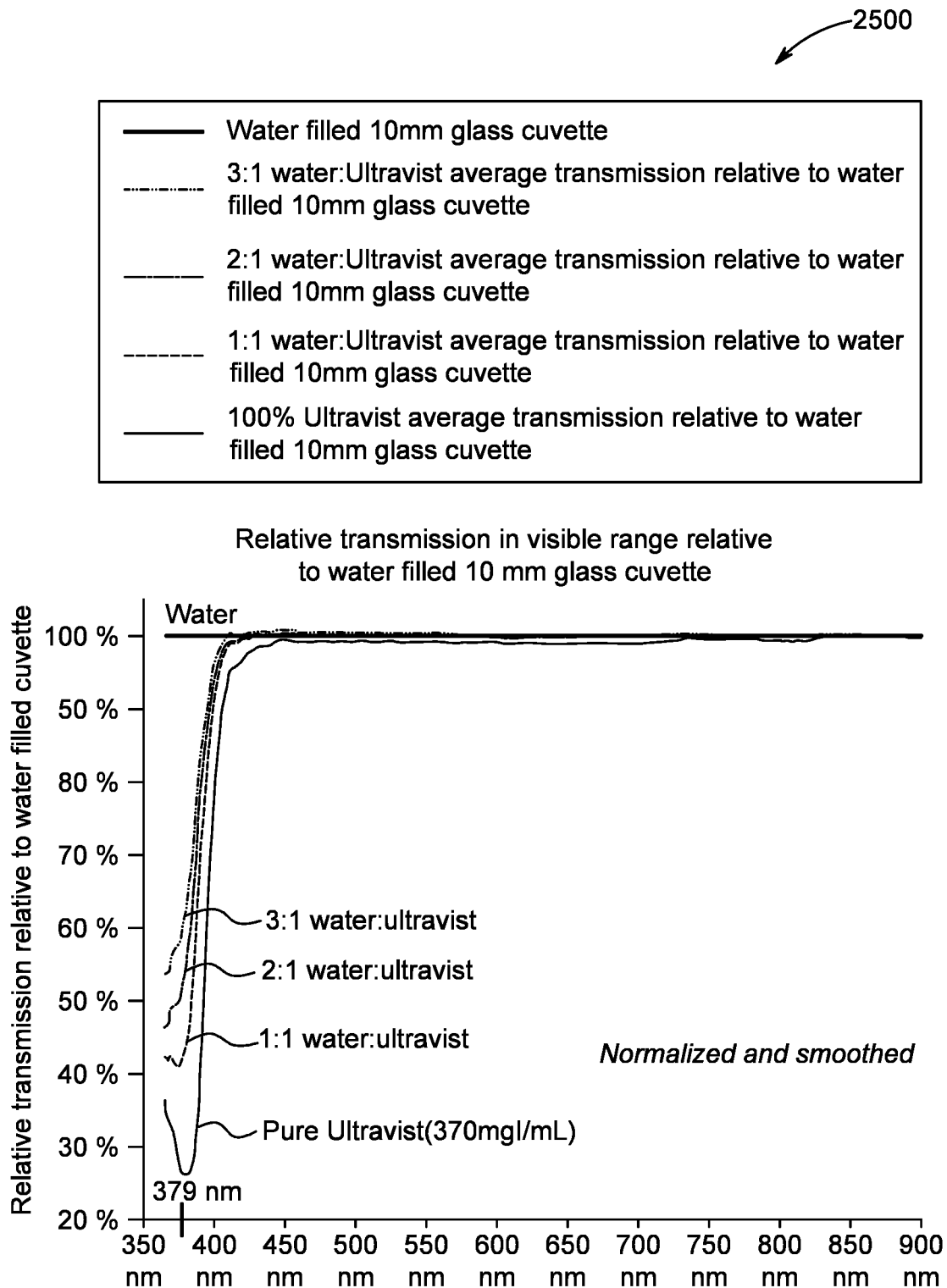
FIG. 12 is a graph of relative electromagnetic transmission for various contrast media in a fluid path section, according to an embodiment of the present disclosure.

Referring to FIGS. 12-15, graphs 2500-2800 illustrate various empirically observed transmission percentages for electromagnetic radiation through various commercially available contrast media solutions as a function of wavelength generated by the emitter 312. Referring first to FIG. 12, graph 2500 shows experimental data gathered for relative transmission of electromagnetic radiation through various dilutions of Ultravist® 370 contrast media in a 10 millimeter (mm) glass cuvette. Transmission of electromagnetic radiation through water in a 10 mm glass cuvette is also shown as a baseline value, with essentially 100% transmission rate. The graphed dilutions include pure Ultravist® 370 and ratios of 1:1, 2:1, and 3:1 water to Ultravist® 370. As can be appreciated from graph 2500, the greatest differentiation in relative transmission between the various dilutions occurs in or near the UV spectrum, for example at a region from 370 to 390 nm, and in particular approximately 379 nm in this embodiment.

The difference in relative transmission at a given wavelength can be used to differentiate between saline (similar to water) and contrast, and between the various dilutions of contrast with water. In particular, the detector 314 detects the electromagnetic radiation transmitted through the fluid in the fluid path section 570, so differences in transmission percentages of the various dilutions result in different amounts of electromagnetic radiation reaching the detector 314. Consequently, the resulting output signal generated by the detector 314 will be different for water and contrast dilutions having different transmission percentages at a given wavelength. By using an emitter 312 emitting electromagnetic radiation at a predetermined wavelength, for example at approximately 379 nm, the controller 900 may be able to determine approximately which dilution ratio of Ultravist® 370 is present in the fluid path section 570) based on the output signal of the detector 314. In particular, the controller 900 may be configured to match the output voltage of the detector 314 to known output voltages associated with various dilutions of Ultravist® 370. In some embodiments, the controller 900 may be configured to reference a database of known output voltages associated with various dilutions. In some embodiments, the controller 900 may be configured to interpolate a dilution ratio of Ultravist® 370 based on the output voltage of the detector 314.

Figure 13:
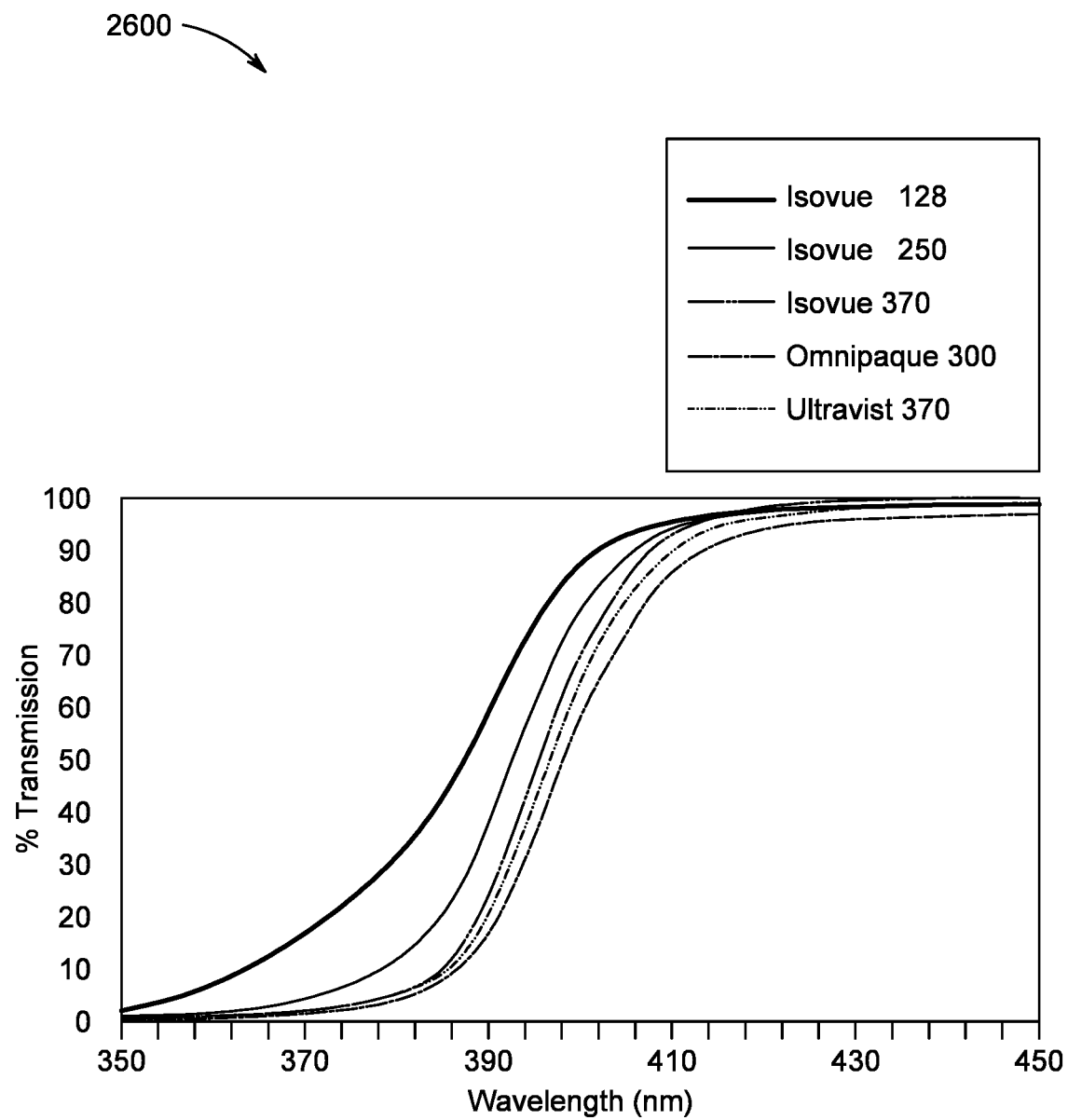
FIG. 13 is a graph of relative electromagnetic transmission for various contrast media in a fluid path section, according to an embodiment of the present disclosure.
Figure 14:
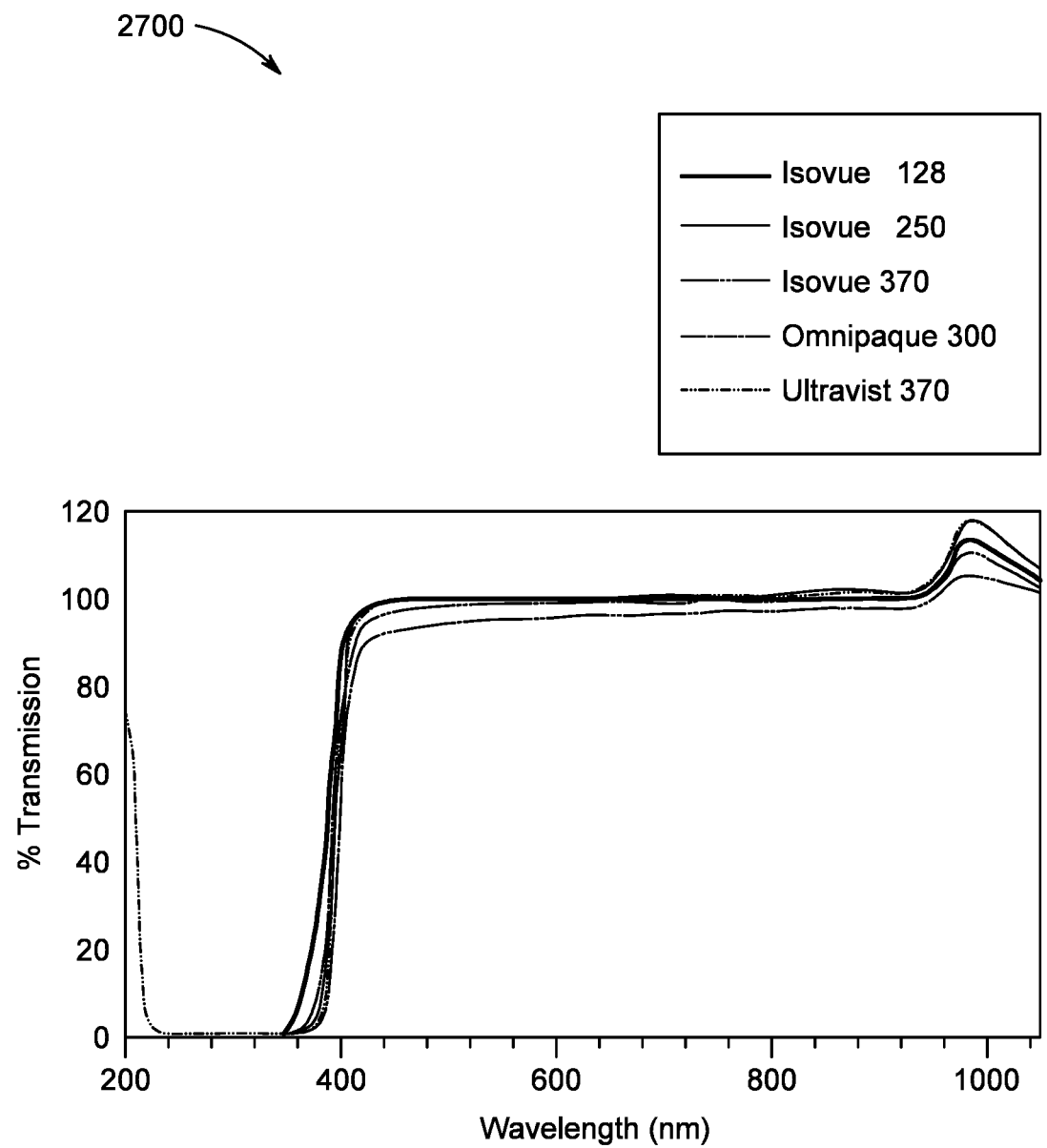
FIG. 14 is a graph of relative electromagnetic transmission for various contrast media in a fluid path section, according to an embodiment of the present disclosure.
Figure 15:
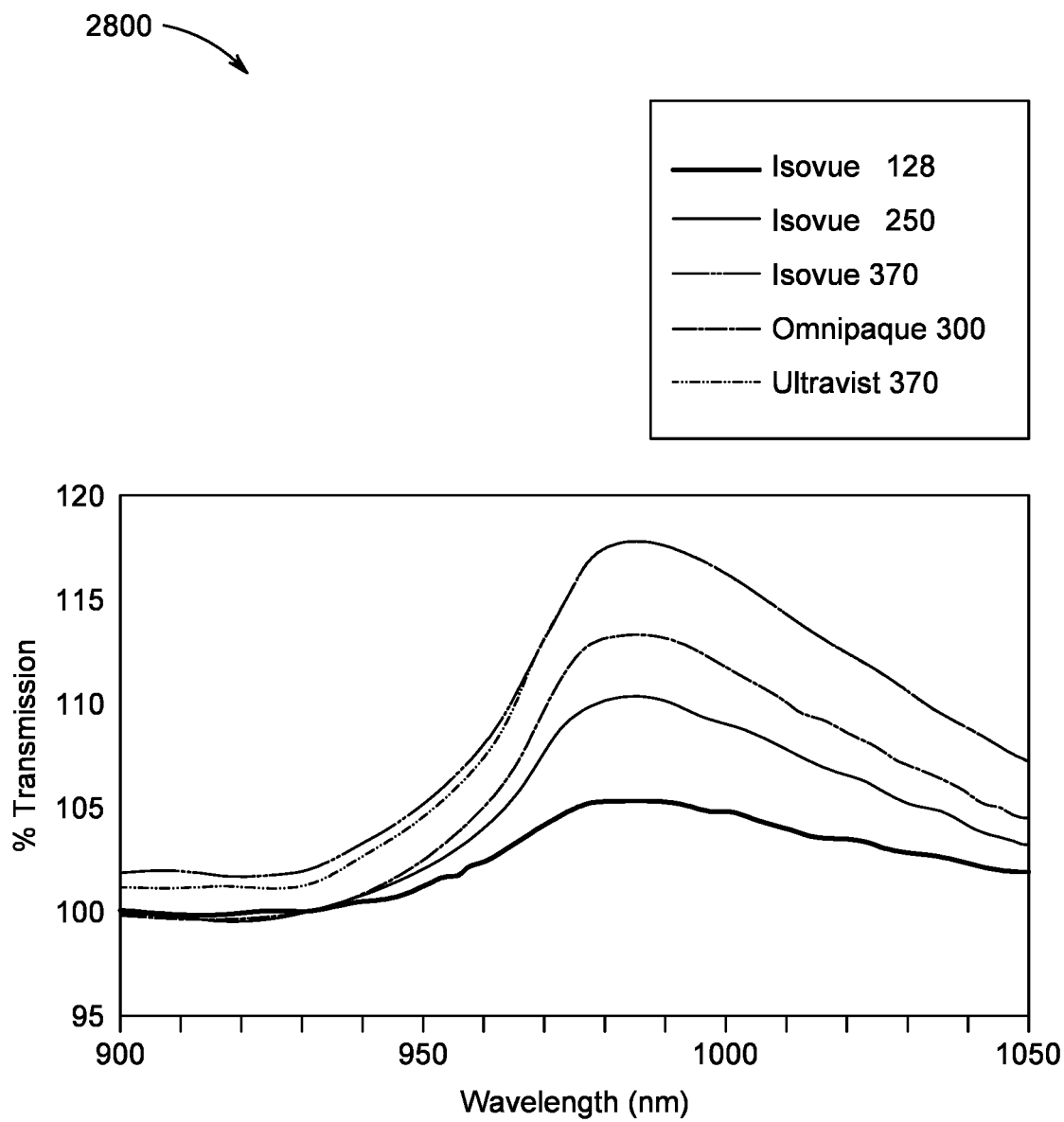
FIG. 15 is a graph of relative electromagnetic transmission for various contrast media in a fluid path section, according to an embodiment of the present disclosure.

Referring to FIG. 13, graph 2600 shows transmission percentage of electromagnetic radiation with wavelengths falling between 350 and 450 nm through various commercially available contrast media solutions including Isovue® 128, Isovue® 250, Isovue® 370, Omnipaque™ 300, and Ultravist® 370. Graph 2700 of FIG. 14 shows the same data as graph 2600 but expanded for electromagnetic radiation with wavelengths falling between about 200 and about 1020 nm. Graph 2800 of FIG. 15 shows transmission percentage of the same commercially available contrast media solutions for electromagnetic radiation with wavelengths falling between 900 nm and 1050 nm. As noted in FIG. 12, the difference in relative transmission at a given wavelength may be used to differentiate between the various contrast media solutions. As can be appreciated from FIGS. 13-15, the greatest differentiation in transmission percentage of the various contrast media solution may occur in or near the infrared and ultraviolet regions of the electromagnetic spectrums. Thus, the emitter 312 may be configured to generate electromagnetic radiation in or near the infrared and ultraviolet spectrums to take advantage of this differentiation. In other embodiments, the emitter 312 may be configured to generate electromagnetic radiation in the visible spectrum. In other embodiments, the emitter 312 may be able to generate electromagnetic radiation at two or more different wavelengths, such as two wavelengths within the infrared region of the electromagnetic spectrum, two wavelengths within the ultraviolet region of the electromagnetic spectrum, or at a wavelength in the infrared region and a wavelength in the ultraviolet region of the electromagnetic spectrum. Accordingly, the emitter 312 may pulse electromagnetic radiation at different wavelengths through the fluid path section 570 to gather several absorption/transmission data points on the fluid in the fluid path section 570 to more accurately determine the identity of the fluid within the fluid path section 570. In some embodiments, the controller 900 may be configured to determine which of the contrast media solutions is present in the fluid path section 570 based on the output signal of the detector 314. In particular, the controller 900 may be configured to match the output voltage of the detector 314 to known output voltages associated with various commercially available contrast media solutions. In some embodiments, the controller 900 may be configured to reference a database of known output voltages associated with various commercially available contrast media solutions.

Figure 16:
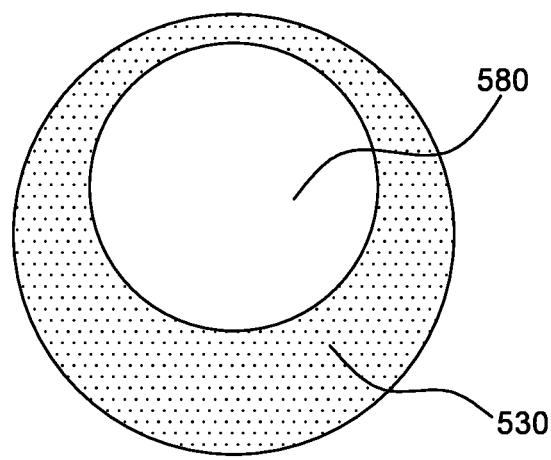
FIG. 16 is a front cross-sectional view of an eccentric fluid path section.
Figure 17:
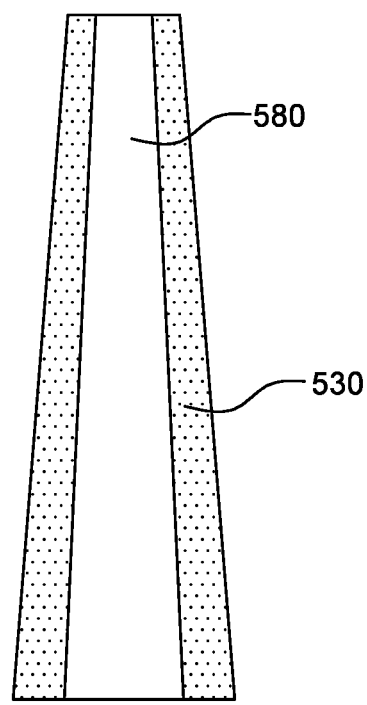
FIG. 17 is a side cross-sectional view of a fluid path section having a draft.
Figure 18:
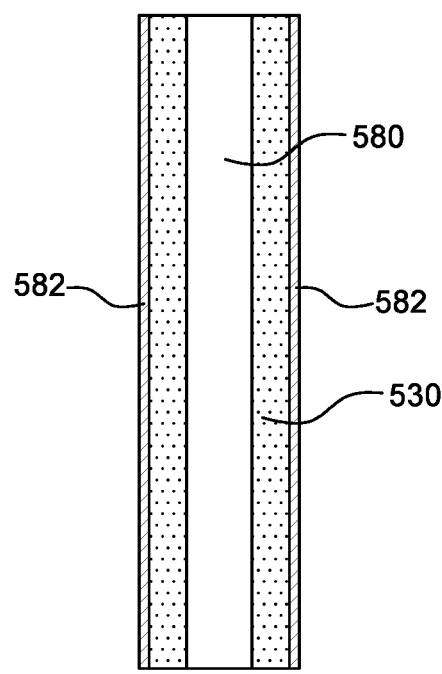
FIG. 18 is a side cross-sectional view of a fluid path section having a surface finish.
Figure 19:
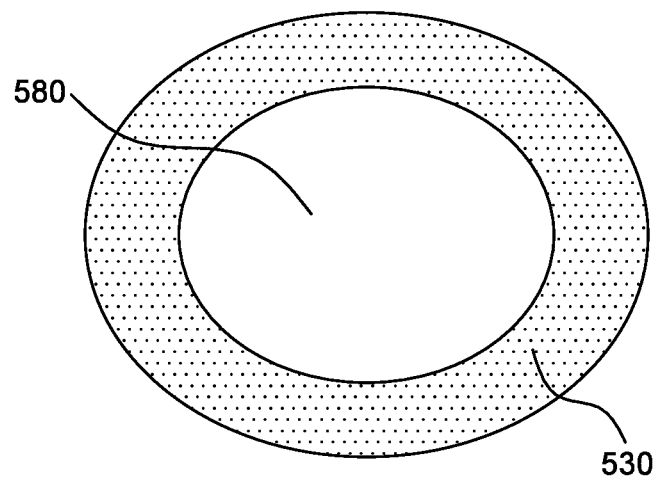
FIG. 19 is a front cross-sectional view of an out-of-round fluid path section.
Figure 20:
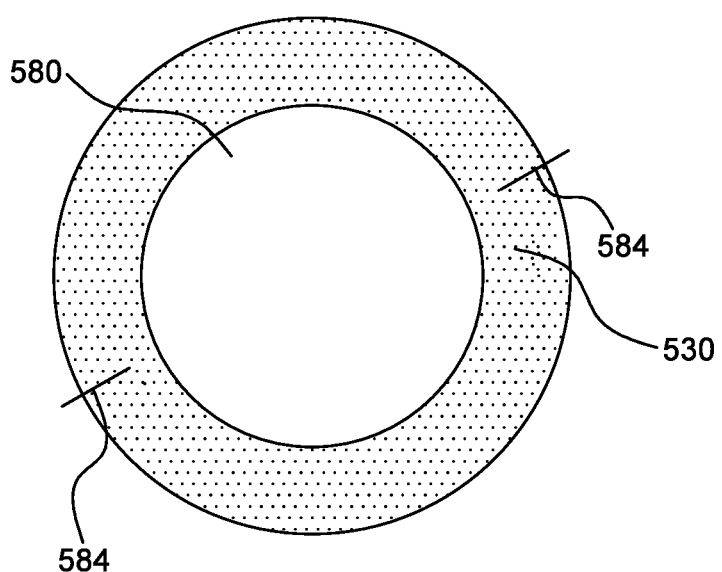
FIG. 20 is a front cross-sectional view of a fluid path section having a wisp.

Referring to FIGS. 16-20, various tubing geometries and manufacturing defects which may be present in the fluid path section associated with the sensor 310 are shown. FIG. 16 shows an eccentricity in which a lumen 580 of the fluid path section is not concentric with the sidewall 530. FIG. 17 shows a draft in which the inner diameter and/or outer diameter of the sidewall 530 tapers in a proximal-to-distal direction. FIG. 18 shows a surface finish 582 applied to the sidewall 530. As described herein, certain surface finishes may be intentional to manipulate the convergence and/or divergence of the electromagnetic radiation passing through the sidewall 530. However, other surface finishes and/or inconsistently applied surface finished may adversely affect sensor readings. FIG. 19 shows an oval tube in which the inner diameter and/or outer diameter of the sidewall 530 are out of round. FIG. 20 shows a wisp 584 in the sidewall 530, for example an inclusion in the base material or a molding line imparted during manufacturing. Each of the features shown in FIGS. 16-20 may cause the electromagnetic radiation passing through the fluid path section to behave in unexpected ways, which can result in spurious and unreliable output signals from the detector 314. In empirical testing, differentiating between types of contrast media requires the most sensitivity, and as such the types of tubing irregularities shown in FIGS. 16-20 may have the most pronounced influence in this type of differentiation. Alternatively, differentiating between air and contrast media, air and saline, and contrast media and saline required less sensitivity, so tubing irregularities of FIGS. 16-20 may have lesser or negligible effects on these determinations.

In some embodiments, the controller 900 may be configured to perform a test measurement prior to the injection and/or syringe filling procedure to establish the presence of and potential effects of these geometry features/defects on the output signals from the detectors 314. The controller 900 may use the results of the test measurement to calibrate the detector 314 and/or to calculate one or more correction factors based in the effects of the features/defects in one or both the contrast injection fluid paths and the flushing fluid paths. During the filling and/or injection procedure, the controller 900 may apply the correction factor to the output signals from the detector 314 to compensate for the manufacturing feature/defects.

An additional manufacturing issue that can affect sensor readings is the inner diameter of the sidewall 530 being different from an expected value. This can occur due to manufacturing tolerances and/or the use of third party fluid path set components. An unexpected inner diameter of the sidewall 530 can particularly effect air bubble volume calculations, as the controller 900 may utilize a predetermined diameter constant corresponding to the inner diameter to convert the detected length of the air bubble into a volume. If the actual inner diameter of the sidewall 530 is different than predetermined diameter constant, the calculation of air bubble volume may be inaccurate. In some embodiments, the controller 900 may be configured to perform a test measurement prior to the injection procedure to establish the sidewall outer diameter, inner diameter, and thickness based on the detected refraction of the empty fluid path section. Based on the test measurement, the controller 900 may apply a correction factor to subsequent output signals from the detectors 314.

Figure 21A:
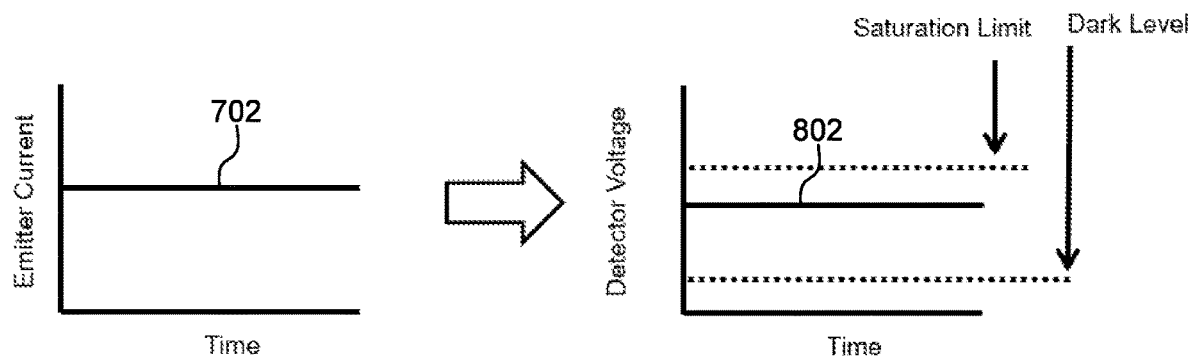
FIGS. 21A-21H are graphs showing detector output voltage as a function of emitter current, according to embodiments of the present disclosure.
Figure 21B:
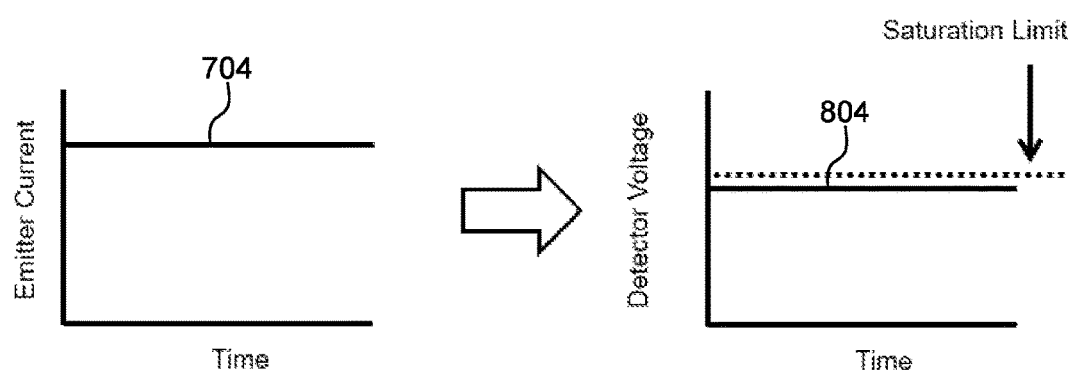
Figure 21C:
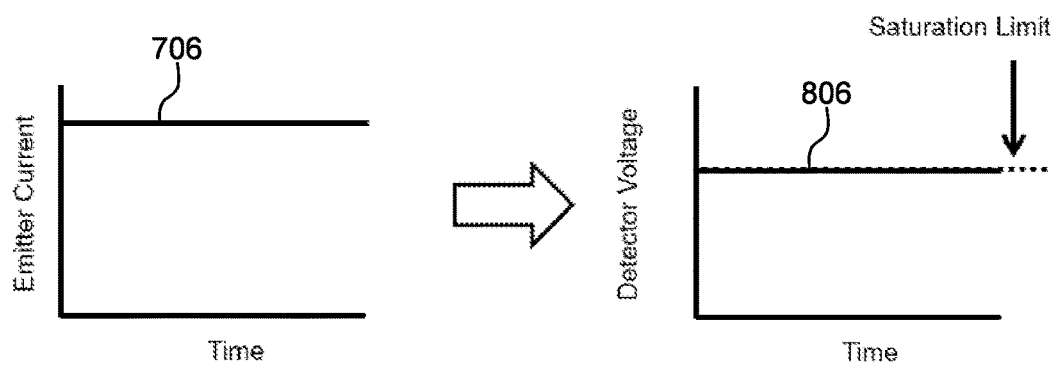
Figure 21D:
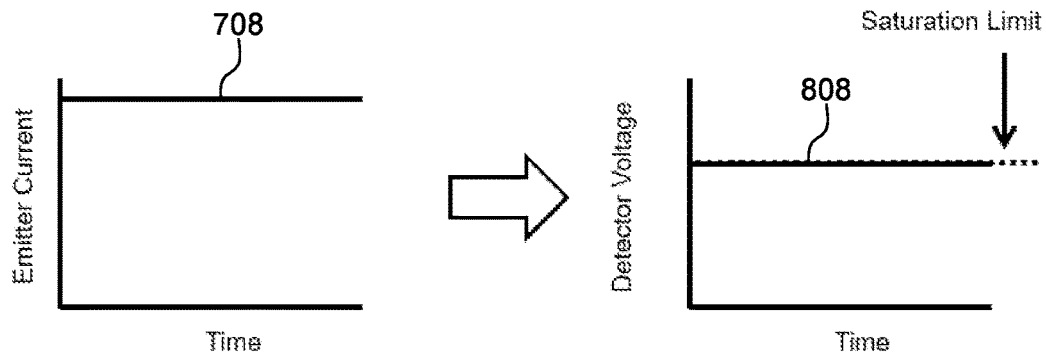

Referring to FIGS. 21A-21H, in some embodiments, the controller 900 may be configured to manipulate the intensity and/or wavelength of the electromagnetic radiation generated by the emitter 312 to enhance the sensitivity and/or gather additional information from the sensor 310. In particular, the controller 900 may increase the current to the emitter 312, causing the emitter 312 to emit light at a high intensity, or decrease the current to the emitter 312, causing the emitter 312 to emit light at a lower intensity. In some embodiments, the controller 900 may power the emitter 312 at a predetermined intensity known to saturate the detector 314. When the detector 314 is at its saturation limit, the output voltage of the detector 314 is at a maximum, and a further increase in the intensity of light from the emitter 312 will not produce a higher output voltage from the detector 314. FIGS. 21A-21D illustrate detector output voltage as a function of emitter current for an arbitrary embodiment of the sensor 310. As shown in FIG. 21A, the detector 314 has a dark level, corresponding to minimum output voltage, and a saturation limit, corresponding to a maximum output voltage. FIG. 21A illustrates a first emitter current 702, selected to produce a first detector output voltage 802 between the dark level and the saturation limit of the detector 314. FIG. 21B illustrates a second emitter current 704 that is greater than the first emitter current 702, consequently causing the detector 314 to produce a second detector output voltage 804 greater than the first output voltage 802. In this case, the second detector output voltage 804 is still below the saturation limit of the detector 314. FIG. 21C illustrates a third emitter current 706 that is greater than the second emitter current 704, consequently causing the detector 314 to produce a third detector output voltage 806 greater than the second detector output voltage 804. In this case, the third emitter current 706 produces sufficient light intensity that the detector 314 is saturated, and thus the third detector output voltage 806 is at the saturation limit. FIG. 21D illustrates a fourth emitter current 708 that is greater than the third emitter current 706. As the detector 314 has already reached its situation limit, a fourth detector output voltage 808 produced by the fourth emitter current 708 is substantially equal to the third detector output voltage 806. Further increases in the emitter current will likewise not result in an increase in output voltage of the detector 314.

Figure 21E:
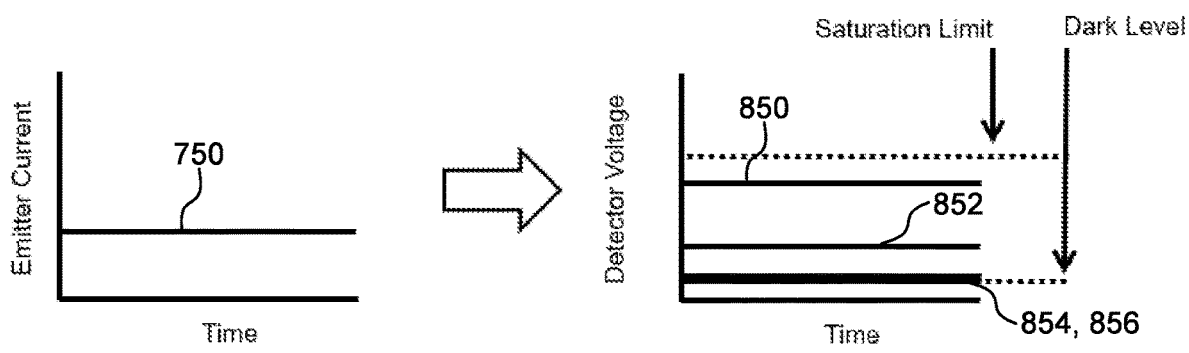

The saturation limit for a given detector 314 is substantially constant. Because the refraction and absorption characteristics of the contents between the emitter 312 and detector 314 affect the amount and/or intensity of light that reaches the detector 314, the refraction and absorption characteristics of the fluid in the fluid path section (and the fluid path section itself) will determine the emitter current required to reach the saturation limit of the detector 314. The controller 900 may utilize the known saturation limit of the detector 314 to differentiate between fluids, e.g. air, saline, and contrast, and to differentiate between types and/or concentrations of contrast. For example, the controller 900 may drive the emitter 312 with a current that would be sufficient to saturate the detector 314 if only air was present in the fluid path section. If the detector output voltage does in fact reach the saturation limit in response to this emitter current, the controller 900 may determine that only air is present in the fluid path section. However, if the detector output voltage does not reach the saturation limit in response to this emitter current, the controller 900 may determine that another fluid is present. In some embodiments, the controller 900 may continue to modulate the current to the emitter 312 to further deduce the type and/or concentration of fluid in the fluid path section. For example, the controller 900 may drive the emitter 312 with a current that would be sufficient to saturate the detector 314 if the fluid in the fluid path section included less than a predetermined ratio of contrast to saline. If the detector output voltage reached the saturation limit in response to this emitter current, the controller 900 may determine that the fluid in the fluid path section has less than the predetermined ratio of contrast to saline FIGS. 21E-21H illustrate this method of determining fluid content of the fluid path section by incrementally increasing emitter current. In FIG. 21E, the controller 900 drives the emitter 312 at a fifth emitter current 750, corresponding to a known current that will not saturate the detector 314 even if only air is present in the fluid path section. At this emitter current, a detector output voltage associated with air 850, a detector output voltage associated with a first contrast solution 852, a detector output voltage associated with a second contrast solution 854, and a detector output voltage associated with a third contrast solution 856 are all below the saturation limit of the detector 314. Nevertheless, the detector output voltage associated with air 850 is sufficiently differentiated from the detector output voltages associated with the contrast solutions 852, 854, 856 that the controller 900 may be able to conclude, based on the actual measured detector output voltage of the detector 314, that air is present in the fluid path section. It is noted that at the fifth emitter current 750), detector output voltages associated with the second contrast solution and the third contrast solution 854, 856 are substantially at the dark level of the detector 314, and therefore controller 900 cannot effectively differentiate between the second and third contrast solutions 854, 856 at the fifth emitter current 750.

Figure 21F:
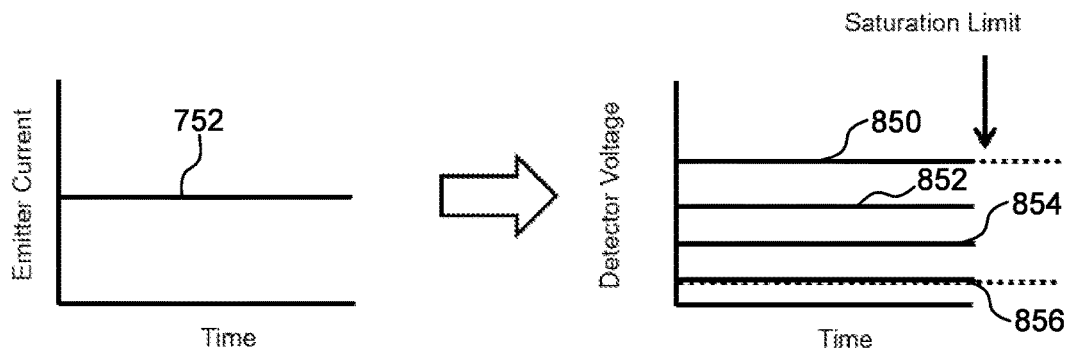

Referring to FIG. 21F, the controller 900 may increase the current to the emitter 312 in order to improve the ability to differentiate between the fluids, particularly the first, second, and third contrast solutions 852, 854, 856. To do so, the controller 900 may drive the emitter 312 at a sixth emitter current 752 greater than the fifth emitter current 750. At the sixth emitter current 752, the detector output voltage associated with air 850 is at the saturation limit of detector 314. The detector output voltage associated with the second contrast solution 854 has moved out of the dark level and is therefore within the effective resolution of the detector 314. At the sixth emitter current 752, controller 900 may be able to differentiate between particularly the first and second contrast solution 852, 852, based on the actual output voltage of detector 314. Further, by a method of elimination, contrast solution 856 may be eliminated as if still falls within the dark level.

Figure 21G:
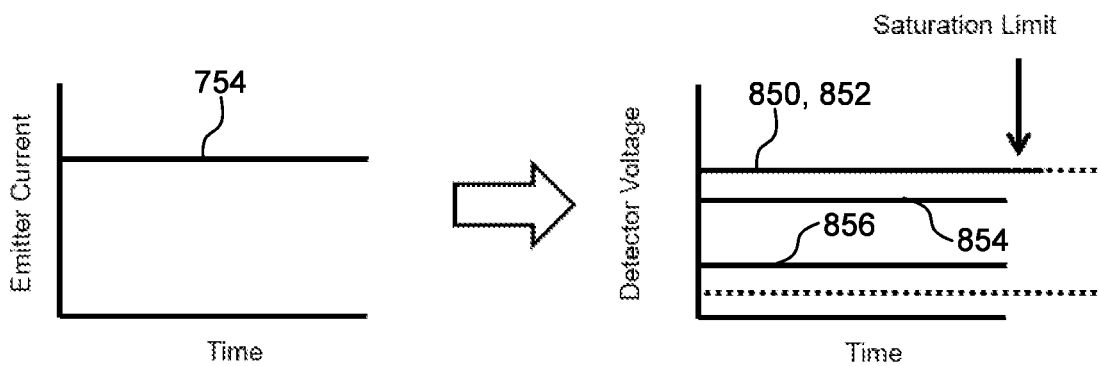
Figure 21H:
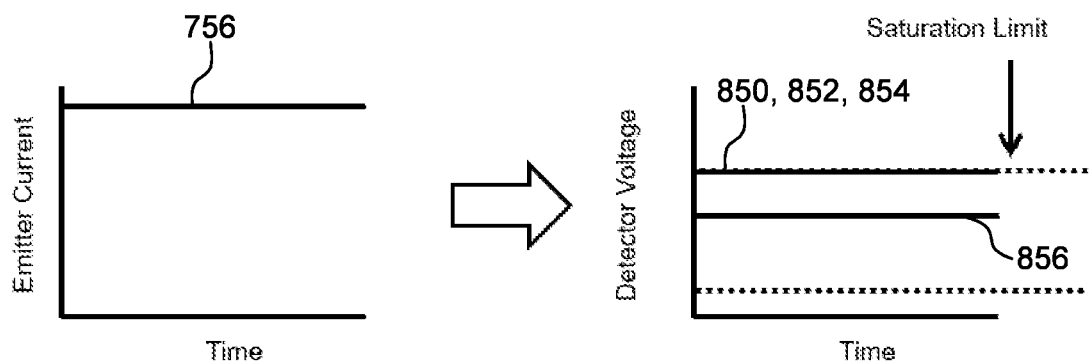

Referring to FIG. 21G, the controller 900 may again increase the current to the emitter 312 in order to improve the ability to differentiate between the fluids, particularly the second and third contrast solutions 854, 856. At a seventh emitter current 754, the detector output voltages associated with air 850 and first contrast solution 852 are at the saturation limit of the detector 314. The detector output voltage associated with the third contrast solution 856 has moved out of the dark level. In addition, the spread between the detector output voltages associated with the second and third contrast solution 854, 856 has increased, making differentiation between the second and third contrast solution 854, 856 easier and/or more reliable at the seventh emitter current 754 compared to the sixth emitter current 752.

The controller 900 may again increase the current to the emitter 312 to an eighth emitter current 758. At the eight emitter current 758, the detector output voltages associated with air 850, first contrast solution 852, and second contrast solution 854 are at the saturation limit of the detector 314. Thus, controller 900 may be able to determine that the third contrast solution 856 is present in fluid path section if the actual detector output voltage of detector 314 is any value below the saturation limit. Controller 900 may be configured to incrementally modulate the current diving the emitter 312 at predetermined time intervals to analyze the fluid content of the fluid path section as described in connection with FIGS. 21A-21H.

Figure 22:
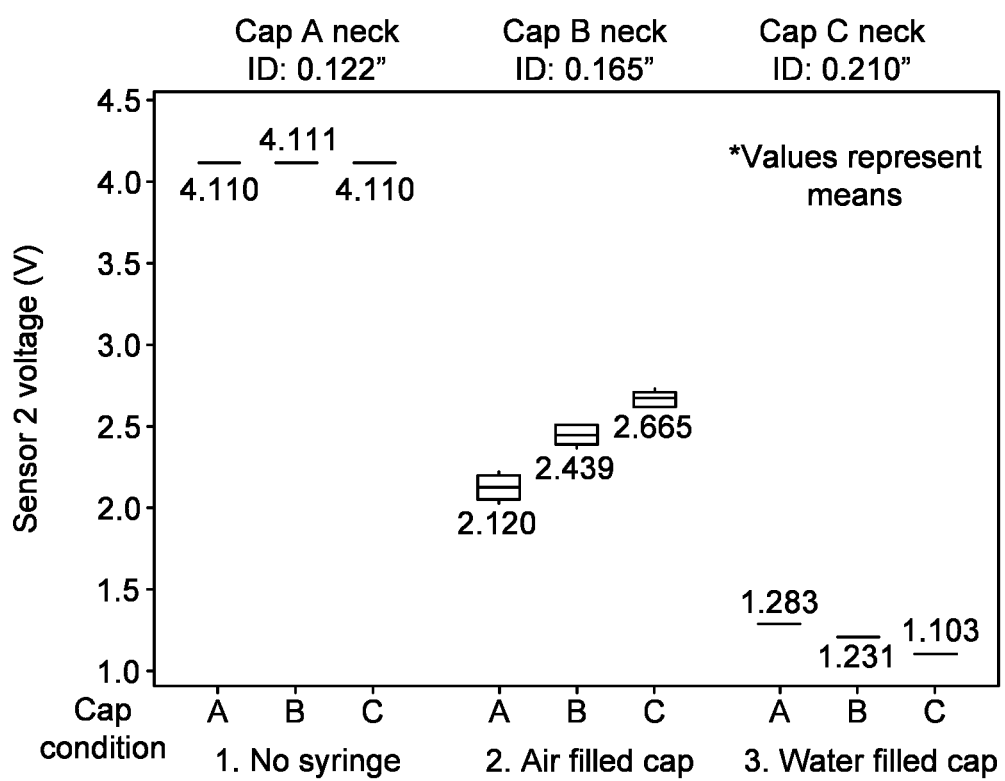
FIG. 22 is a graph of sensor output voltage over time for various conditions and configurations of a syringe cap.

Referring to FIG. 22, a graph of exemplary output signals of the detector 314 is shown for the sensor 310 arranged in operative association with syringe tips 16A, 16B (as shown in FIG. 7 or FIG. 24) of three difference internal diameters (Syringe cap "A" of 0.122 inches, Syringe cap "B" of 0.165 inches, and Syringe cap "C" of 0.210 inches). Tests were performed for each of Syringe Caps "A", "B", and "C" for three different conditions: the syringe cap not in operative association with the sensor module 300A, 300B; the syringe cap in operative association with the sensor module 300A, 300B and filled with air; and the syringe cap in operative association with the sensor module 300A, 300B and filled with water. The output signals from the detector 314 allow the controller 900 to discriminate between these three conditions regardless of the internal diameter of the syringe cap. Across measurements taken for all three syringe cap diameters, the mean output signals for the syringe cap not in operative association with the sensor ranged from 4.110 to 4.111 volts; the mean output signals for the syringe cap filled with air ranged from 2.120 to 2.665 volts; and the mean output signals for the syringe cap filled with water ranged from 1.102 to 1.283 volts. For the test results shown in FIG. 22, the emitter 312 operated at a wavelength of 1450 nm.

While various examples of the present invention were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid injector system, comprising:
   at least one injector for pressurizing and delivering at least one fluid from a first fluid reservoir and a second fluid reservoir;
   a first fluid path section providing fluid communication between a first bulk fluid container and the first fluid reservoir and a second fluid path section providing fluid communication between a second bulk fluid container and the second fluid reservoir, wherein the first fluid reservoir is a first syringe connected to the at least one injector and the second fluid reservoir is a second syringe connected to the at least one injector;
   a first sensor arranged along the first fluid path section and a second sensor arranged along the second fluid path section, each of the first sensor and the second sensor comprising an emitter and a detector,
      wherein a first emitter associated with the first sensor and a second emitter associated with the second sensor are configured to emit light through the first fluid path section and the second fluid path section, respectively; and
      wherein a first detector associated with the first sensor and a second detector associated with the second sensor are configured to receive the light emitted through the first fluid path section and the second fluid path section, respectively, and generate an electrical signal based on at least one property of the received light; and
   at least one processor programmed or configured to determine, based on the electrical signal generated by the first detector or the second detector, at least one of:
      an identity of the at least one fluid present in at least one of the first fluid path section and the second fluid path section;
      a concentration of the at least one fluid in at least one of the first fluid path section and the second fluid path section; and
      at least one property of at least one of the first fluid path section and the second fluid path section, and
   wherein the at least one processor is programmed or configured to determine, based on the electrical signals generated by the first and second sensors, that the fluid filling the first fluid reservoir was originally intended by an injection protocol to fill the second fluid reservoir; and the fluid filling the second fluid reservoir was originally intended by the injection protocol to fill the first fluid reservoir, and
   adjust the injection protocol to ensure that injection parameters are updated to switch the identity of the first fluid reservoir and the second fluid reservoir so that first fluid is associated with the first fluid reservoir and the second fluid is associated with the second fluid reservoir.

2. The fluid injector system of claim 1, wherein the emitter is arranged on a first side of the at least one of the first fluid path section and the second fluid path section,
   wherein the detector is arranged on a second side of the at least one of the first fluid path section and the second fluid path section, and
   wherein the second side of the at least one of the first fluid path section and the second fluid path section is approximately 180° opposite the first side of the at least one of the first fluid path section and the second fluid path section.

3. The fluid injector system of claim 1, wherein the at least one processor is programmed or configured to alter the injection protocol by configuring the first fluid reservoir to inject the fluid originally intended by the injection protocol to be injected by the second fluid reservoir and configuring the second fluid reservoir to inject the fluid originally intended by the injection protocol to be injected by the first fluid reservoir.

4. The fluid injector system of claim 3, wherein the at least one processor is programmed or configured to adjust a display of a graphical user interface or to illuminate a first light source associated with the first fluid reservoir and a second light source associated with the second fluid reservoir to indicate that the first fluid reservoir contains the fluid originally intended by the injection protocol to be injected by the second fluid reservoir, and that the second fluid reservoir contains the fluid originally intended by the injection protocol to be injected by the first fluid reservoir.

5. The fluid injector system of claim 1, wherein the least one processor is programmed or configured to determine, based on at least one of identity of the at least one fluid and a concentration of the at least one fluid in the at least one of the first fluid path section and the second fluid path section, an optimal fill rate of the at least the first fluid reservoir and the second fluid reservoir.

6. The fluid injector system of claim 1, wherein the first detector and the second detector are each configured to output a first voltage signal when the first fluid path section or the second fluid path section contains contrast media,
   wherein the first detector and the second detector are each configured to output a second voltage signal when the first fluid path section or the second fluid path section contains saline, and
   wherein the at least one processor is programmed or configured to determine the identity of the at least one fluid in the first fluid path section or the second fluid path section based on a difference between the first voltage signal and the second voltage signal.

7. The fluid injector system of claim 6, wherein the first detector and the second detector are each configured to output a third voltage signal when the first fluid path section or the second fluid path section contains air, and
   wherein the at least one processor is programmed or configured to determine that air is in the first fluid path section or the second fluid path section based on a difference between the third voltage signal, the first voltage signal, and the second voltage signal.

8. The fluid injector system of claim 7, wherein when the at least one processor determines that air is in the first fluid path section or the second fluid path section, the at least one processor is programmed or configured to provide an alert to a user that at least one of the first bulk fluid container and a second bulk fluid container is empty.

9. The fluid injector system of claim 1, wherein the at least one processor is programmed or configured to:
   determine a concentration of a contrast media in the first fluid path section or the second fluid path section based on the electrical signal generated by the first sensor or the second sensor, and
   either increase a ratio of the injection fluid comprising saline injected during an injection procedure to dilute the concentration of the contrast media delivered to a patient or reduce an injection rate of the injection fluid comprising saline during the injection procedure to increase the concentration of the contrast media delivered to the patient.

10. The fluid injector system of claim 1, wherein the at least one processor is programmed or configured to determine, based on the electrical signal, that the first fluid path section or the second fluid path section are present between the first emitter and the first detector of the first sensor or the second emitter and the second detector of the second sensor.

11. The fluid injector system of claim 1, wherein the first emitter and the second emitter are each configured to emit light on at least one of an ultraviolet spectrum, an infrared spectrum, and a visible spectrum.

12. A method for determining one or more fluid properties of an injection fluid flowing in at least one fluid path section of a fluid injector system comprising,
   a first fluid reservoir and a second fluid reservoir for delivering a first injection fluid and a second injection fluid, respectively;
   a first fluid path section of the at least one fluid path section providing fluid communication between a first bulk fluid container of the at least one bulk fluid container and the first fluid reservoir and having a first sensor; and
   a second fluid path section of the at least one fluid path section providing fluid communication between a second bulk fluid container of the at least one bulk fluid container and the second fluid reservoir and having a second sensor, the method comprising:
   emitting light from a first emitter of the first sensor through the first fluid path section and emitting light from a second emitter of the second sensor through the second fluid path section;
   detecting with a first detector of the first sensor the light that has passed through the first fluid path section and detecting with a second detector of the second sensor the light that has passed through the second fluid path section;
   determining, based on an electrical signal generated by the first detector and an electrical signal generated by the second detector, at least one of:
      an identity of the injection fluid present in the first fluid path section and the injection fluid in the second fluid path section; and
      at least one property of the first fluid path section and the second fluid path section; and
   determining, based on the electrical signal generated by the first sensor and the electrical signal generated by the second sensor, whether the injection fluid flowing into the first fluid reservoir from the first bulk fluid container was originally intended by an injection protocol to fill the second fluid reservoir; and whether the injection fluid flowing into the second fluid reservoir from the second bulk fluid container was originally intended by the injection protocol to fill the first fluid reservoir; and based on the result, perform at least one of:
      adjusting the injection protocol to ensure that injection parameters are updated to switch the identity of the first fluid reservoir and the second fluid reservoir so that a first injection fluid is associated with the first fluid reservoir and a second injection fluid is associated with the second fluid reservoir; and adjusting the injection protocol by configuring the first fluid reservoir to inject the injection fluid originally intended by the injection protocol to be injected by the second fluid reservoir and configuring the second fluid reservoir to inject the injection fluid originally intended by the injection protocol to be injected by the first fluid reservoir.

13. The method of claim 12, further comprising adjusting a display of a graphical user interface or illuminating a first light source associated with the first fluid reservoir and a second light source associated with the second fluid reservoir to indicate that the first fluid reservoir contains the injection fluid originally intended by the injection protocol to be injected by the second fluid reservoir and that the second fluid reservoir contains the injection fluid originally intended by the injection protocol to be injected by the first fluid reservoir.

14. The method of claim 12, further comprising determining, based on at least one of the identity of the injection fluid and the concentration of the injection fluid in the at least one fluid path section, an optimal fill rate of at least the first fluid reservoir and the second fluid reservoir.

15. The method of claim 12, wherein the first detector and the second detector are each configured to output a first voltage signal when the first fluid path section or the second fluid path section contains the injection fluid comprising contrast media, wherein the first detector and the second detector are each configured to output a second voltage signal when the first fluid path section or the second fluid path section contains the injection fluid comprising saline, and wherein the method further comprises determining the identity of the at least one fluid in the first fluid path section or the second fluid path section based on a difference between the first voltage signal and the second voltage signal.

16. The method of claim 15, wherein the first detector and the second detector are each configured to output a third voltage signal when the first fluid path section or the second fluid path section contains air, and wherein the method further comprises determining that air is in the first fluid path section or the second fluid path section based on a difference between the third voltage signal, the first voltage signal, and the second voltage signal.

17. The method of claim 12 further comprising:
determining a concentration of the injection fluid comprising contrast media in the first fluid path section or the second fluid path section based on the electrical signal generated by the first sensor or the second sensor, and either increasing a ratio of the injection fluid comprising saline injected during an injection procedure to dilute the concentration of the contrast media delivered to the patient; or reducing an injection rate of the injection fluid comprising saline during an injection procedure to increase the concentration of the contrast media delivered to the patient.

18. The method of claim 12, further comprising determining, based on the electrical signal, that the first fluid path section is present between the first emitter and the first detector and the second fluid path is present between the second emitter and the second detector.

19. The method of claim 12, wherein the emitting light from the first emitter and the second emitter comprises emitting light on at least one of an ultraviolet spectrum, an infrared spectrum, and a visible spectrum.

* * * * *